United States Patent [19]

Gleason et al.

[11] 4,257,947

[45] Mar. 24, 1981

[54] 3-AMINO-2-HYDROXY, HALO OR MERCAPTOMETHYL-4-OXOAZETIDINES

[75] Inventors: John G. Gleason, Delran; Kenneth G. Holden, Haddonfield, both of N.J.; William F. Huffman, Malvern, Pa.

[73] Assignee: SmithKline Corporation, Philadelphia, Pa.

[21] Appl. No.: 20,293

[22] Filed: Mar. 14, 1979

Related U.S. Application Data

[60] Division of Ser. No. 821,386, Aug. 3, 1977, Pat. No. 4,166,816, which is a continuation-in-part of Ser. No. 696,094, Jun. 14, 1976, Pat. No. 4,072,674, which is a continuation-in-part of Ser. No. 626,686, Oct. 29, 1975, abandoned, which is a continuation-in-part of Ser. No. 574,225, May 5, 1975, abandoned.

[51] Int. Cl.$^3$ .................. C07D 205/08; C07D 403/04
[52] U.S. Cl. ................................................. 260/239 A
[58] Field of Search ................................... 260/239 A

[56] References Cited

U.S. PATENT DOCUMENTS

| 3,943,123 | 3/1976 | Bose | 260/239 A |
| 4,068,075 | 1/1978 | Menard et al. | 260/239 A |
| 4,122,086 | 10/1978 | Hall et al. | 260/245.4 |
| 4,144,333 | 3/1979 | Hall et al. | 260/326 S |

FOREIGN PATENT DOCUMENTS 2046823  3/1972  Fed. Rep. of Germany ...... 260/239 A

OTHER PUBLICATIONS

Gleason et al., Chem. Abs. 86, 106617x (1975).

*Primary Examiner*—Mark L. Berch
*Attorney, Agent, or Firm*—William H. Edgerton; Richard D. Foggio; Alan D. Lourie

[57] ABSTRACT

The stereospecific cycloaddition of nitrogen containing acetic acid halides or anhydrides with Schiff bases having a carbalkoxy group substituted on the methine carbon atom offers new intermediates and methods for preparing synthetic cephalosporin congeners having antibacterial activity.

6 Claims, No Drawings

3-AMINO-2-HYDROXY, HALO OR MERCAPTOMETHYL-4-OXOAZETIDINES

This is a division of application Ser. No. 821,386, filed Aug. 3, 1977, now U.S. Pat. No. 4,166,816, which is a continuation-in-part of application Ser. No. 696,094, filed June 14, 1976, now U.S. Pat. No. 4,072,674, which in turn is a continuation-in-part of our application Ser. No. 626,686, filed Oct. 29, 1975, now abandoned, which is a continuation-in-part of our application Ser. No. 574,225, filed May 5, 1975, now abandoned.

This invention relates to cephalosporin-like compounds which have antibacterial activity and to chemical compounds and methods useful to prepare these novel antibacterial agents.

BACKGROUND

Cephalosporins obtained by fermentation processes or ring expansion of penicillins all contain the 8-oxo-5-thia-1-azabicyclo[4.2.0]oct-2-ene nucleus, i.e.

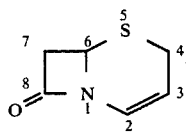

Compounds with this ring system have been the object of intense research and numerous scientific articles and patents. As a result of this effect, approximately eight commercial products are available today as antibacterial agents.

Analogous rings systems in which the sulfur atom has been moved to another position in the six-membered ring can not be obtained by the same methods as described for the above nucleus. A totally synthetic approach to this ring system must be employed. One system which has been attempted with varied success is the 8-oxo-4-thia-1-azabicyclo[4.2.0]octane for which the trival name isocephalosporin can be given, i.e.

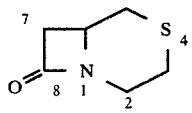

The synthesis of 7β-phenylacetamido-7α-methyl-6αH-8-oxo-4-thia-1-azabicyclo[4.2.0]oct-2-ene-2-carboxylic acid and the 2,3-dihydro derivative has been reported in *J. Chem. Soc.* 1321 (1973). These compounds lack the 2-3 double bond believed necessary for biological activity and/or have a 7α-methyl group which is not present in naturally occurring cephalosporins. These two compounds were reported to have no antibacterial activity when tested at high levels against three bacteria. Also reported within this reference was a derivative with trans-configuration, 7α-phenylacetamido-6αH-8-oxo-4-thia-1-aza-[4.2.0]octane-2-carboxylic acid. This compound also showed no activity. Within this reference attempts to prepare the nucleus without the methyl substituent and with the 2-3 double bond were unsuccessful. Further attempts were reported in *J. Chem. Soc. Perkin I*, 2092 (1974) and were also unsuccessful.

We have now prepared the 6,7αH-8-oxo-4-thia-1-azabicyclo[4.2.0]oct-2-ene ring system; in particular, 7β-acylamino-6αH-8-oxo-4-thia-1-azabicyclo[4.2.0]oct-2-ene-2-carboxylic acids and derivatives thereof.

SUMMARY OF THE INVENTION

The compounds of this invention are represented by the following structural formula:

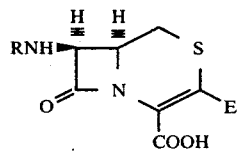

Formula I wherein
R is an acyl group and
E is hydrogen, methyl, bromomethyl, or lower alkanoyloxymethyl.

The term acyl group refers to any acyl group used within the cephalosporin and penicillin art, except phenylacetyl. Preferred acyl groups are represented by the general formulae:

$$X-\underset{A'}{CHCO-}, \quad Y-CH_2-CO-, \quad \text{or} \quad Z-S(O)_nCH_2CO-.$$

Especially preferred acyl groups are those where X is thienyl, cyclohexyl, cyclohexenyl, cyclohexadienyl, phenyl, or phenyl substituted with one or two substituents selected from the group consisting of lower alkyl, lower alkoxyl, hydroxy, hydroxymethyl, halo, nitro, amino, aminomethyl, mercapto, lower alkylthio, trifluoromethyl, ureido, formamido, and carboxymethylamino; A' is amino, hydroxy, formyloxy, carboxyl, or sulfonic acid; Y is cyano, azido, phenoxy or a 5 or 6-membered heterocyclic ring containing 1-4 heteroatoms selected from the group consisting of nitrogen, oxygen and sulfur; Z is phenyl, pyridyl, lower alkyl, trifluoromethyl, trifluoroethyl, or cyanomethyl and n is 0, 1 or 2. The 5 or 6-membered heterocycles include thienyl, furyl, thiazolyl, isothiazolyl, oxadiazolyl, thiadiazolyl, triazolyl, tetrazolyl, sydnone, pyridyl, pyrimidyl and the like. The heterocyclic group may be unsubstituted or substituted with substituents selected from lower alkyl, halo, hydroxy, nitro, amino, lower alkoxy, aryl such as phenyl, lower aralkyl and the like.

The terms lower alkyl, lower alkoxy and lower aralkyl used within this entire disclosure refers to alkyl groups containing one to six carbon atoms. The term halogen or halo includes fluorine, chlorine and bromine.

The compounds which are also a part of this invention and which are useful as intermediates to prepare compounds of Formula I are represented by Formula II:

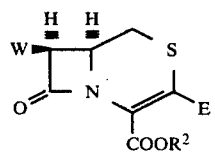

Formula II wherein
E is hydrogen, methyl, bromomethyl or lower alkanoyloxymethyl;
W is R′$_2$N;

R² is hydrogen or removable carboxyl protecting group; and each R' is hydrogen or a monovalent removable amine protecting group or when both R' groups are taken together, a divalent amine protecting group.

Lower alkanoyloxymethyl in both Formulae I and II refers to alkanoyl groups of one to six carbon atoms. A preferred member within this group is acetoxymethyl.

Another group of compounds which are a part of this invention and are useful intermediates for the preparation of the compounds of Formulae I and II are represented by Formula III:

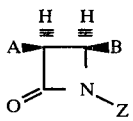

Formula III wherein
A is $N_3$, $NH_2$, acylamino, or protected amino;
B is COOY or $CH_2X'$;
Y is hydrogen or lower alkyl;
X' is OM, halogen, p-methoxybenzylthio, triphenylthio, or mercapto;
M is hydrogen, lower alkylsulfonyl or phenylsulfonyl, said phenyl being unsubstituted or substituted with methyl or halogen; and
Z is hydrogen or 2,4-dimethoxybenzyl.

The term "removable carboxyl protecting group" is a term which has acquired a definite meaning within the cephalosporin and organic chemical arts. Many groups, particularly many ester groups, are known which are used to protect the carboxyl groups during subsequent chemical reactions and later removed by standard methods to give the free carboxylic acid group. Known ester protecting groups include 2,2,2-trichloroethyl, $C_4$–$C_6$-tert-alkyl, such as t-butyl, $C_5$–$C_7$-tert-alkenyl, $C_5$–$C_7$-tert-alkynyl, $C_1$–$C_6$-alkanoylmethyl, N-phthalimidomethyl, benzoylmethyl, halobenzoylmethyl, methylbenzoylmethyl, methanesulfonylbenzoylmethyl, phenylbenzoylmethyl, benzyl, nitrobenzyl, methoxybenzyl, benzhydryl, trityl, trimethylsilyl, triethylsilyl and the like. The choice of which ester group to use is well within the ability of one skilled in the art. Factors which are considered include what subsequent reaction conditions the group must withstand and what conditions for removing the protecting ester is desirable. Groups which are removed by treatment with trifluoroacetic acid, hydrogenation or zinc dust and acetic acid have been preferred in the art when a β-lactam is fused to a six-member ring. The choice of the protecting group is not critical to our invention since the novelty of our invention lies within the new bicyclic nuclei and not the ester substituents.

A "removable amine protecting group" or a "protected amino group" are terms well known in the art. They refer to amino groups which have been masked by another group so as to protect them during subsequent chemical reactions and then the masking group can be removed to generate again the desired amino moiety. Many groups are known and used for this purpose within the penicillin, cephalosporin, and peptide synthetic arts. Examples of these include, t-butoxycarbonyl, trichloroethoxycarbonyl, benzyloxycarbonyl, p-methoxybenzylcarbonyl, isobornyloxycarbonyl, trityl, methyl acetoacetate adduct and the like which are monovalent protecting groups. Divalent protecting groups include phthaloyl and the 4,5-diphenyl-4-oxazolin-2-one group. Treatment of a phthalimido group with hydrazine by published procedures cleaves the phthaloyl group to regenerate the amino group. Preparation and removal of the 4-oxazolin-2-one group is taught in the art; J. Org. Chem., 38, 3034 (1973). The choice of the protecting group depends on various factors including the subsequent chemical reaction conditions and the desired conditions for removal of the protecting group. However, this choice is within the ordinary ability of one skilled in the art. Again the choice of the amino protecting group is not critical to our invention for the same reasons given above about the carboxyl protecting group.

The term acyl group means any acyl group which has been used in the semisynthetic penicillin and cephalosporin fields except phenylacetyl including the following examples:
α-hydroxyphenylacetyl
α-formyloxyphenylacetyl
α-aminophenylacetyl
α-amino-4-hydroxyphenylacetyl
α-amino-4-hydroxy-3-fluorophenylacetyl
α-amino-4-carboxymethylaminophenylacetyl
trifluoromethylmercaptoacetyl
methylmercaptoacetyl
methylsulfonylacetyl
2,2,2-trifluoroethylsulfinylacetyl
cyanoacetyl
cyanomethylmercaptoacetyl
cyanomethylsulfinylacetyl
cyanomethylsulfonylacetyl
α-carboxy-2-thienylacetyl
α-carboxy-3-thienylacetyl
α-carboxyphenylacetyl
α-sulphophenylacetyl
3-sydnoneacetyl
2-thienylacetyl
3-thienylacetyl
1-tetrazolylacetyl.

The compounds of this invention set forth in Formulae I and II contain a nucleus which is related to naturally occurring cephalosporins but which cannot be prepared by fermentation methods. Therefore, the compounds are prepared by a totally synthetic route as outlined in Scheme I. Within Scheme I, R is any acyl group as set out above or a derivative thereof in which any chemically sensitive group such as carboxy, hydroxy or amino is protected with a standard removable protecting group, many of which have been described above, until the final step of the reaction sequence. Many protective groups are set forth in the book "Protective Groups in Organic Chemistry", ed. J. F. W. McOmie, Plenum Press, New York, 1973 and in other review articles and books. R' is an amino protecting group which is removed after the 4-thia-1-azabicyclo[4.2.0]-oct-2-ene nucleus is formed to give the 7-amino derivative. This derivative can then be acylated by the same standard methods used within the cephalosporin art with the desired acyl group to give the compounds of this invention. R² is a protective ester residue used to protect the carboxyl group and is also removable at the end of the reaction sequence to give the final active products which contain a free carboxyl group or a salt thereof.

SCHEME I

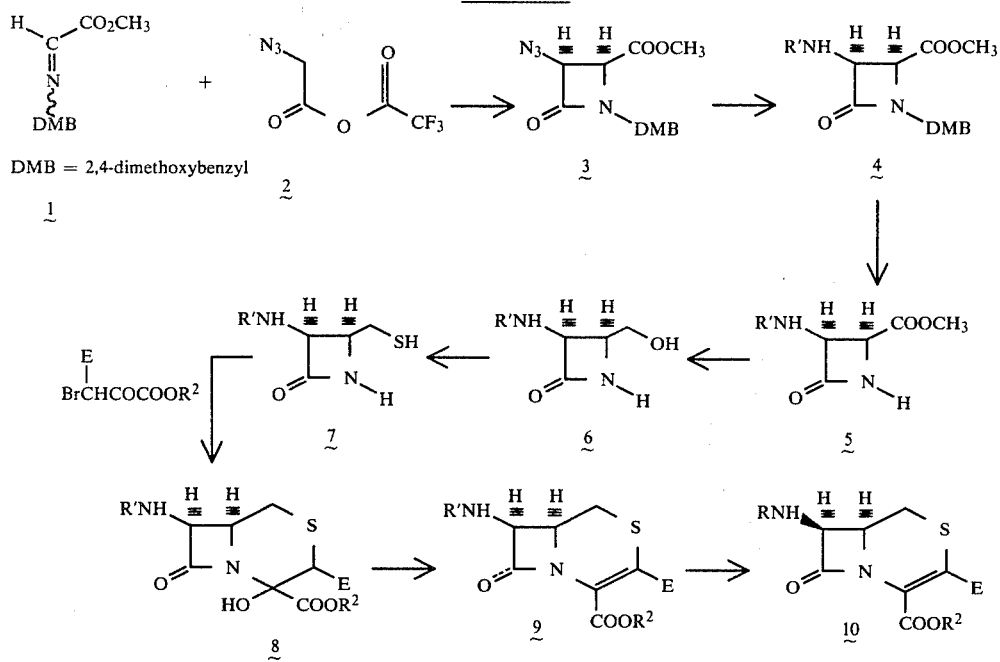

DMB = 2,4-dimethoxybenzyl

The important intermediate which gives the new nucleus its 6,7-cis configuration is methyl cis-1-(2,4-dimethoxybenzyl)-3-azido-4-oxoazetidine-2-carboxylate (3). This compound is prepared by the cycloaddition reaction between the imine obtained from the condensation of 2,4-dimethoxybenzylamine and methyl glyoxalate and a mixed anhydride or acid halide of azidoacetic acid. The azido group of this intermediate is reduced by catalytic hydrogenation or by chemical reduction such as zinc and acetic acid to give the 3-aminoazetidine derivative. The amino group can be protected by a removable amino protecting group such as t-butoxycarbonyl. A protected 3-aminoazetidine derivative can also be prepared directly by substitution of a glycine derivative in which the amino group has been protected. For example, 4,5-diphenyl-2-oxo-4-oxazolin-3-ylacetic acid or N-phthalimidoacetic acid can be used in the cyclization reaction in the same manner as azidoacetic acid to give the corresponding protected 3-aminoazetidine derivative.

The intermediate 3 or a protected 3-aminoazetidine described above can be converted by a series of reactions into the 2-methylsulfonate derivative as illustrated by compound 11 in Scheme II. Varied reaction sequences can be used in the preparation of compounds like 11 Scheme II sets forth two alternate pathways which can be used to go from compound 3 to compound 11. It is apparent to persons skilled in the art that conversion of the azido group to the protected amino is not limited to the two illustrated places along the reaction sequence but can also be done at other alternative places. Reduction of the azido moiety is advantageously done on compound 3 in Scheme II or on the 3-azido-2-methyl tosylate derivative 12.

The methylsulfonate derivative (11) is then converted stepwise to the mercaptomethyl derivative 7 as set forth in Scheme III. The sulfonate is displaced with iodide in which is in turn displaced with a mercaptan derivative such as p-methoxybenzyl mercaptan or triphenylmethyl mercaptan. Cleavage of these derivatives by standard synthetic methods gives the mercaptomethyl compound 7. The p-methoxybenzyl group is cleaved by treatment with mercuric salts. The triphenylmethyl group is cleaved by treatment with silver salts including silver nitrate and silver tetrafluoroborate and therefore is advantageous if other groups within the compound are sensitive to mercuric ion.

SCHEME II

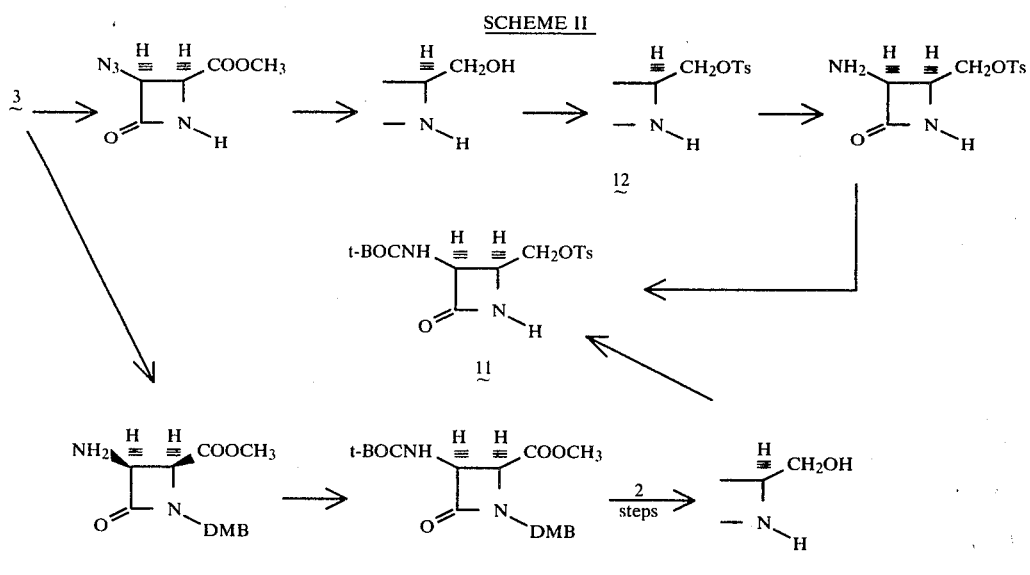

t-BOC = t-butoxycarbonyl; Ts = tosyl

The mercaptomethyl compound 7 is reacted with a β-bromo-α-keto ester to give the bicyclic system as shown in compound 8. When a bromopyruvate ester is used, compound 8 where E is hydrogen is obtained. When a 3-bromo-2-ketobutyrate ester is used, compound 8 where E is methyl is obtained. These compounds are dehydrated to give the 8-oxo-4-thia-1-azabicyclo[4.2.0]oct-2-ene system 9. Standard dehydration reagents such as thionyl chloride, trifluoroacetic anhydride, and methanesulfonyl anhydride are used.

Compounds of structure 9 where E is bromomethyl are prepared by radical bromination of the 3-methyl compounds using the procedures known in the cephalosporin art. Bromination reagents include N-bromosuccinimide in the presence of radical initiators such as benzoyl peroxide or azobisisobutyronitrile.

The bromomethyl derivatives can be reacted with various acetic salts to give compounds of structure 9 where E is acetoxymethyl. Exemplary salts useful for this purpose include sodium, potassium, or silver acetate.

Compounds of structure 10, the antibacterial agents of this invention, are prepared from compounds of structure 9 by removal of the amino protecting group followed by acylation with the desired acyl group using standard acylation methods. Following the acylation any additional protecting groups are removed. During the acylation reaction any sensitive groups such as amino or hydroxy are protected as has been previously described. Standard acylation methods include activation of the carboxyl by use of mixed anhydrides, activated esters, and acid halides or by use of coupling reagents such as dicyclohexylcarbodiimide.

Some compounds within the scope of Formula I can alternatively be prepared by acylation with the desired acyl group earlier in the reaction sequence. For example, the 3-aminoazetidone derivative can be prepared and acylated at the same places as those disclosed in Scheme II. When this acylated monocyclic β-lactam is carried along the reaction sequence herein disclosed the desired final products are obtained. Examples of acyl groups for which this alternate method can be used include phenoxyacetyl, α-aminophenylacetyl, α-amino-p-hydroxyphenylacetyl, 2-thienylacetyl and the like.

More specifically, when 2,4-dimethoxybenzylamine [Chem. Ber., 101, 3623 (1968)] is condensed with methyl glyoxalate [Synthesis, 544 (1972)], imine 1 is obtained. Reaction of this imine with the mixed anhydride of trifluoroacetic acid and azidoacetic acid [Tetrahedron Lett., 2319 (1973)] gives methyl cis-1-(2,4-dimethoxybenzyl)-3-azido-4-oxo-2-azetidinecarboxylate (3). This reaction can be run as a two-step process by first generating the mixed anhydride and then adding this to a solution of the imine. Alternatively, a one step procedure can be used in which the azidoacetic acid is added to a solution of the imine followed by the addition of the trifluoroacetic anhydride. In addition, other glyoxalate esters such as ethyl or propyl can be used in the same manner.

The 2,4-dimethoxybenzyl group is removed by oxidative methods. For example, treatment of the N-(2,4-dimethoxybenzyl)β-lactam with potassium persulfate effects the deblocking reaction to generate the free β-lactam. This reaction is carried out in the presence of sodium monohydrogen phosphate. With some derivatives, pH control during the reaction within a range of 5-6 may be advantageous to the reaction yield. Under these conditions we have found that the benzyl group is not removed like the dimethoxybenzyl group. However, one skilled in the art could try other substituted benzyl moieties and determine if they are removable and therefore are also able to perform the same function as the dimethoxybenzyl group.

Reduction of the 2-alkoxycarbonyl group with suitable reducing agents such as sodium borohydride gives the 2-methyl alcohol derivative. In particular, the methoxycarbonyl group is readily reduced with sodium borohydride to give the alcohol derivative.

The alcohol derivative can also be prepared by reduction of the 2-carboxylic acid by standard reduction methods known in the art. The acid is prepared from the ester derivative by base hydrolysis. For example, the methyl ester hydrolyzes to the carboxylic acid by treatment with sodium carbonate, potassium carbonate or similar base. The carboxylic acid can be converted to its acid chloride and reduced with sodium borohydride to give the desired alcohol moiety. The 1-(2,4-dimethoxybenzyl)-2-carboxylic acid derivatives can be reduced to the 2-methyl alcohol derivative which can be converted to the corresponding tosylate. The dimethoxybenzyl group can be removed at this point to give the β-lactam methyl tosylate precursor which can be carried further as has been described.

The alcohol is treated with p-toluenesulfonyl chloride, benzenesulfonyl chloride, p-bromobenzenesulfonyl chloride, mesyl chloride or similar reagents which convert the alcohol into a group which is readily displaced by iodide ion by nucleophilic displacement. Standard nucleophilic displacement of the sulfonate moiety with iodide followed by another nucleophilic displacement with sulfur derivatives gives the mercapto methyl moiety or a group which can be converted to the desired mercapto methyl compound. Triphenylmethylmercapto and p-methoxybenzylmercapto are typical groups which readily cleaved to the free mercapto group as set out above.

The new cephalosporin-like nucleus is generated by a cyclization reaction of the mercaptomethyl compound and a bromopyruvate derivative. The product formed contains a hydroxy group alpha to the carboxyl group. Dehydration of this hydroxy group places the double bond in the nucleus at the 2,3-position analogous to the cephalosporin series. Dehydration is best carried out with thionyl chloride or trifluoroacetic anhydride and pyridine.

The starting materials for the compounds of this invention are commercially available, prepared by known methods or described herein.

Also included within the scope of this invention is the pharmaceutically acceptable non-toxic salts of the active compounds or esters easily degraded to the active compound in vivo. These include the salts of the carboxylic acid at position 2 or within the acyl sidechain and the acid addition salts of any basic substituent present in the compound. Carboxylic acid salts include those where the cation is an alkali metal such as sodium or potassium, alkaline earth such as calcium, or an ammonium cation such as ammonium, cyclohexylamine and the like. The acid addition salts are prepared from those acids known and used in pharmaceutical preparations including both inorganic and organic acids. The salts are prepared by the standard methods well-known in the art.

The compounds of this invention within Formulae I and II exist in the cis configuration at positions 6 and 7. The compounds also exist as optical isomers. Included within the scope of this invention is the separate optical isomers as well as any mixtures thereof.

The compounds of Formula I of this invention have antibacterial activity against both Gram-positive and Gram-negative bacteria. For example, 7-phenoxyacetamido-8-oxo-4-thia-1-azabicyclo[4.2.0]oct-2-ene-2-carboxylic acid has antibacterial activity against *Staphylococcus aureus* and *Shigella paradysenteriae*. The compound 7-(α-aminophenylacetamido)-8-oxo-4-thia-1-azabicyclo[4.2.0]oct-2-ene-2-carboxylic acid has additional activity against *Escherichia coli, Klebsiella pneumoniae, Serratia marcescens, Salmonella paratyphi, Shigella paradysenteriae,* and Enterobacter species. The 2-thienyl congener is also very active. The compounds are useful for the treatment and prevention of bacterial infections as well as for sterilization of equipment, glassware and the like. Further details are available in our copending application Ser. No. 693,992, filed June 8, 1976 now U.S. Pat. No. 4,103,086.

The compounds of Formulae II and III are useful as chemical intermediates in the preparation of novel cephalosporin-like compounds of Formula I as has been described herein. Compounds within Formula II where W is amino (NH$_2$) can be acylated as described above with any of the acyl groups known in the cephalosporin or penicillin arts to give compounds which, after removal of any ester protecting group, have antibacterial activity. Compounds within Formula II where R' is an amino proprotecting group are useful to prepare the compounds where R' is hydrogen.

The compounds claimed here are the valuable intermediates of Formula III above with the groups at Y and Z expanded to include equivalent groups as will be disclosed herein. The compounds of key subgeneric groups are the compounds (a) in which B is carbalkoxy (that is, for example, B is

lower alkyl); (b) in which B is carbalkoxy and Z is 2,4-dimethoxybenzyl; (c) in which B is carbalkoxy and Z is hydrogen; or (d) in which B is tosyloxymethyl and Z is hydrogen.

Individual compounds of this part of the invention which are particularly useful are those of Formula III in which:

A is azido, B is carbethoxy and Z is 2,4-dimethoxybenzyl;

A is azido, B is carbethoxy and Z is hydrogen;

A is azido, B is carbomethoxy and Z is 2,4-dimethoxybenzyl;

A is azido, B is carbomethoxy and Z is hydrogen;

A is amino, B is carbomethoxy and Z is 2,4-dimethoxybenzyl;

A is amino, B is carbomethoxy and Z is hydrogen;

A is phthalimido, B is carbomethoxy and Z is 2,4-dimethoxybenzyl;

A is phthalimido, B is carbomethoxy and Z is hydrogen;

A is azido, B is tosyloxymethyl and Z is hydrogen;

A is phenoxyacetamido, B is carbomethoxy and Z is hydrogen;

A is tert.-butoxycarbonylamino, B is carbomethoxy and Z is hydrogen;

A is azido, B is hydroxymethyl and Z is hydrogen;

A is tert.-butoxycarbonylamino, B is mercaptomethyl and Z is hydrogen;

A is 4,5-diphenyl-2-oxo-4-oxazolin-3-yl, B is carbomethoxy and Z is hydrogen.

The intermediates of Formula III are distinguished by being exclusively cis-4-oxo-azetidines as noted above. Also included where appropriate are the salt derivatives often used standardly in synthetic procedures. That is acid addition salts where basic amine function is present, such as hydrohalide, tosylate, acetate, mesylate, sulfate, nitrate, etc., or alkali metal salts such as the sodium or potassium salt if an acidic function such as carboxylic acid is present. As far as we are aware, the cis-4-oxo-azetidines claimed herein are novel. Belgian Pat. No. 772,940 discloses a process for preparing a large number of azetidinones using an ozonolysis reaction but the preparation of the starting materials for the process is unclear. The configuration of the end product is predominantly in the unfavorable trans position. No carbalkoxy esters at the 2-position are specifically mentioned in this reference. Also U.S. Pat. No. 3,943,123 discloses certain carboxy aryl or aralkylazetidines but no stereospecific formation of the desired cis-series.

Also a part of the invention claimed here are two key chemical reactions. The first of these is a cyclization to give a cis-azetidinone by reacting a carbalkoxyl containing imine (1a) with a reactive acyl halide or mixed anhydride formed from an azidoacetic acid (2a). In place of the azido radical one can alternatively use a "protected", or "blocked" amino or an "acylamino" as described herein:

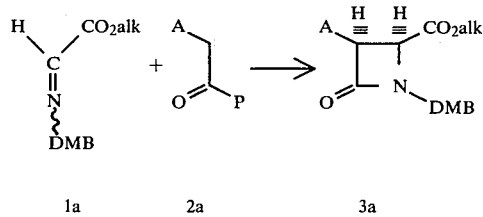

in which alk is lower alkyl of 1-6 carbon atoms but substituted or unsubstituted, straight or branched as defined hereafter such as methyl, ethyl, trichloroethyl or benzyl; DMB is 2,4-dimethoxybenzyl or its equivalent; A is azido, "protected" amino or "acylamino"; and P is the halo residue of the acid halide, preferably chloro or bromo, or the reactive portion of the mixed anhydride such as trifluoromethylcarbonyloxy, benzoyloxy, lower alkanoyloxy, lower alkoxycarbonyloxy, benzyloxycarbonyloxy or halo lower alkoxycarbonyloxy. The azido acetic acid chloride or trifluoroacetic acid mixed anhydride reagents are preferred reactants for 2a. The acid chloride reagents are of particular use for the protected amino or acylamino containing 2a reagents.

The term "protected" amino defines any group which masks or blocks the undesired chemical vulnerability of the amino function during reaction but which is readily removed when desired. Many such are known to the polypeptide or antibiotic arts. Exemplary are tert.-butoxycarbonylamino (t.boc), trichloroethoxycarbonylamino, benzyloxycarbonylamino, p-methoxybenzylcarbonylamino, isobornyloxycarbonylamino, tritylamino, benzhydrylamino, methylacetoacetate imino adduct, phthalimido, succinimido, maleimido, 4,5-diphenyl-2-oxo-4-oxazolin-3-yl, 2,6-dimethoxybenzoylamino or p-nitrobenzoylamino.

Suitably protected "acylamino" acetyl chlorides or anhydrides which can be used for this invention include those listed herebefore. Exemplary of these are the starting materials in which compound 2a is phenoxyacetylaminoacetyl chloride, O-benzylmandeloylaminoacetyl chloride (which gives cis-3-mandeloylamino-2-carbomethoxy-4-oxoazetidine after cyclization followed by catalytic hydrogenation of the protective O-benzyl group), D-α-tert.-butoxycarboxamidophenylacetamido acetic acid (reacted as the mixed anhydride with isobutylchloroformate, then the t.-boc group split using trifluoroacetic acid as in U.S. Pat. No. 3,867,380), O-formylmandeloylaminoacetylchloride, cyanoacetamidoacetyl chloride or N-methyl-1-tetrazolylacetamidoacetyl chloride.

It should be understood that the term "acylamino" is used solely for describing such pharmaceutically acceptable groups known to the cephalosporin art at the 7-position or their known synthetic precursors. These are distinct from "protective" groups whose sole function is to protect the amine function during cyclization or oxidative degradation.

In the term "protected amino" advantageous compounds in regard to yield of the cycloaddition reaction are those with amino substituents in which both amino hydrogens are replaced in effect with bifunctional or bivalent protecting groups. Exemplary of these bifunctionally protected amino groups are phthalimido, succinimido, maleimido or 4,5-diphenyl-2-oxo-4-oxazolin-3-yl. The monovalent or monofunctional protective groups as well as the "acylamino" groups as defined above undergo cycloaddition with heavy formation of by-products and in very low yields of β-lactam containing material. These compounds are best prepared by standard reaction with the 3-aminoazetidinone derivative in the reaction sequence. That is with the 3-aminoacetidinone after the cycloaddition reaction.

The "alk" portion of the structures presented herebefore as in 1a, 3a or Formula III as a portion of the carbalkoxy substituent in the Schiff and on the subsequently formed 4-oxoazetidines represents part of any easily removed ester moiety. For convenience it is a branched or unbranched aliphatic chain of from 1–6 carbon atoms which may be optionally substituted by conventional substituents in the art such as halos or phenyl. Since the group is eliminated in the later steps of the synthetic sequence wide variability is possible but not necessary for the reaction overall. Most useful are the carbomethoxy and carbethoxy moieties but "alk" may be any aliphatic moiety derived from the alk glyoxate starting material for example trichloroethyl, n-butyl, isoamyl, benzyl, methoxybenzyl, phenethyl, t-butyl, benzhydryl, isopropyl, etc.

The cycloaddition of imines or Schiff bases and azidoacetic acid in the form of its acid chlorides or anhydrides is known to the art [for example the work of A. K. Bose et al., Tetrahedron, 23, 4769 (1967) up to Tetrahedron Letters, 22, 1917 (1974) especially Tetrahedron Letters 26, 2319 (1973) and U.S. Pat. No. 3,943,123]. Most of the reported cycloadditions have one or more aromatic substituents in the imine reactant. The addition most often favors forming the undesirable trans azetidine or a mixture of cis-trans isomers. In certain cyclic or highly substituted series cis addition has been reported, J. Org. Chem. 29, 3632 (1964).

As far as we know the use of phenyl or benzyl imines or Schiff bases (or azomethines) which have a carbalkoxy group substituted on the methine carbon atom is novel to give exclusively cis-azetidinones. Also the ability to remove the N-benzyl substituent from the azetidinones in one oxidative step is novel.

The cycloaddition reaction comprises reacting the imine (1a) with the reactive acid halide or mixed anhydride (2b) in an aprotic solvent wich is inert under the reaction conditions and in which the reactants are reasonably soluble. For example, the solvent may be a chloro-containing hydrocarbon such as methylene chloride, carbon tetrachloride or chloroform; an aromatic solvent as benzene or toluene; tetrahydrofuran; dioxane; dimethylsulfoxide; hexamethylphosphoramide; ethyl acetate; acetonitrile; ether; dimethylformamide or dimethylacetamide; or mixtures thereof. The solvent is not critical but methylene chloride is often used. The reaction temperature may be from just above the freezing point of the mixture up to room temperature. Certain reactions may be run at about −30° to −80° C. Most useful are temperatures of from about −30° to 5° C. The reaction may take from about one-quarter to eight hours. Most often the reaction is run in an ice bath for several hours.

As noted the cyclization reaction to produce the monovalently protected or acyl containing azetidine amino compounds generally speaking gives lower yields than it does using the azido-containing or bivalently protected amino acetic acid derivative. The latter reaction is, therefore, a most useful one.

The second key reaction is the removal of the N-dimethoxybenzyl group from the azetidone compounds of Formulae 3, 3a or 4:

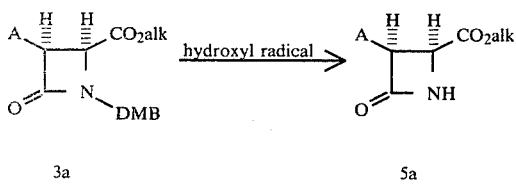

The term DMB is used to define the very useful 2,4-dimethoxybenzyl N-substituent. For the good yield aralkyl N-substituents having a potentially very stable free radical form is necessary. This is accomplished by more than one phenyl substituent such as using the benzhydryl substituent or using electron releasing substituents on the aromatic ring such as methoxy or ethoxy groups or both such as with methoxy substituted benzhydryl. With protective aralkyl groups having potential of forming very stable benzylic type radical forms other splitting reaction conditions can be alternatively used such as with trifluoroacetic acid.

For practical purposes the 2,4-dimethoxy benzyl protective group is most useful. The methoxy groups on the benzhydryl may be at one or more of the two o or p positions of both phenyl rings.

The removal of the N-protective moiety is necessary for conversion of the azetidone compounds to end products having antibacterial activity. The removal of the ring nitrogen substituent is accomplished by the reaction with those oxidizing agents which furnish a hydroxy radical. Organic chemists skilled in synthetic procedures will recognize this class of oxidizing agents. For example, the inorganic persulfates, especially potassium or sodium persulfate, are useful. Alternative splitting reagents may be used for example the organic peracids, such as perbenzoic or peracetic acid or N-bromosuccinimide or in some instances trifluoroacetic acid.

The solvent for the splitting reaction is any inert solvent in which the reactants are soluble. In the case of the persulfates, acetonitrile, acetone, dioxane or aqueous mixtures thereof are used. The reaction temperature may vary from room temperature to the reflux temperature of the mixture. A useful range is from about 60°–100° C. Conveniently aqueous acetonitrile at reflux temperature until the reaction is complete may be employed. This is usually from one to eight hours, depending on the scale. The azetidinone starting materials may be monitored during the reaction.

The oxidizing reaction may be applied to any azetidinone bearing a susceptible methoxybenzyl-like blocking group at position 1 as discussed above for example, those of Formula I in which the 1-nitrogen is blocked by a dimethoxybenzyl, benzhydryl or methoxybenzhydryl group. Also the presence of easily oxidized functions such as thiophene in the molecule, for example at the 3-acylamino reaction, may affect the specific course of the oxidation. If such problems arise the 3-acyl moieties must be attached to the ring after debenzylation. Any other susceptible groups such as hydroxyl or amino should be masked as known to the art.

Most conveniently the pH of the oxidation reaction is controlled by any convenient buffer system, for example using sodium acid phosphate systems, boric acid-borax, secondary sodium citrate. The mixture should be close to neutral, say about 5–8 especially about 6.

The reaction proceeds most smoothly with potassium persulfate in aqueous acetonitrile at reflux in a substantially neutral reaction mixture. The N-2,4-dimethoxybenzyl substituent at the 1 or N-position of the 2-carbomethoxy-3-azido-4-oxoazetidine system is removed under these conditions in about 60–70% yield.

One skilled in the art will recognize that the compounds of claim 1 and of Formula III have groups and/or radicals which may not be chemically stable under all conditions and in all environments. Any such conflicting groups may be suitably masked for that compound to serve as an intermediate for further synthesis.

The reaction mixtures of both key reactions are worked up by standard methods as will be evident from the working examples. In the debenzylation aldehyde such as dimethoxybenzaldehyde is generated by the oxidation.

The following are specific embodiments of this invention to teach the invention to those skilled in this art.

PREPARATION 1

Methyl N-(2,4-dimethoxybenzyl)iminoacetate

To a mixture containing 16.82 g (0.101 mole) of 2,4-dimethoxybenzylamine and anhydrous magnesium sulfate in 150 ml of methylene chloride at 25° is added a solution of 10.05 g (0.114 mole) of methyl glyoxalate in 20 ml of methylene chloride. The reaction mixture is stirred at room temperature overnight (15 hours) and then is filtered and the solvents are removed in vacuo to afford the imine as a dark orange gum.

PREPARATION 2

4,5-Diphenyl-2-oxo-4-oxazolin-3-ylacetic acid chloride

A mixture of 4,5-diphenyl-2-oxo-4-oxazolin-3-ylacetic acid (2.1 g, 7.1 mmol) [*J. Org. Chem.*, 38, 3034 (1973)], thionyl chloride (5 ml) and methylene chloride (20 ml) is refluxed for 2.5 hours. After cooling to room temperature the solvent is removed in vacuo and resulting oil crystallizes on standing. The product is triturated with ether-hexane to give the title compound; 2.0 g mp 104°–112°.

PREPARATION 3

Bromopyruvate Esters

To a solution of 3.3 g (37.5 mmole) of pyruvic acid and 7.9 g (37.5 mmole) of trichloroethyl chloroformate in 20 ml of dry tetrahydrofuran at 0° is added dropwise 0.6 ml of pyridine. After stirring for 2 hours at room temperature, the mixture is concentrated in vacuum, diluted with water and extracted with ethyl acetate. The extract is washed with 5% HCl, dried over MgSO$_4$, evaporated and distilled in vacuum to give 4.0 g (50%) trichloroethyl pyruvate, bp 75°–82° (17 mm).

Trichloroethyl pyruvate (3.7 g, 1.7 mmole) is heated to 65° and 1.1 ml (17 mmole) of bromine is added dropwise over 1 hour. A stream of carbon dioxide is passed through the reaction mixture during the addition to remove the HBr formed in the reaction. The mixture is cooled to room temperature, diluted with water and extracted with ethyl acetate. The extract is dried over $MgSO_4$, evaporated and distilled in vacuum to give 1.8 g of trichloroethyl bromopyruvate, bp 74°–77° (0.01 mm).

Bromopyruvic acid is treated with diphenyldiazomethane by standard methods to give benzhydryl bromopyruvate.

The t-butyl ester is also prepared by standard methods of reacting O-t-butyl-N,N'-diisopropylpseudourea [*Ann. Chem.*, 597, 235 (1955)] and bromopyruvic acid.

PREPARATION 4

3-Bromo-2-ketobutyrate esters

At room temperature under argon 1.85 g (9.6 mmol) of diphenyldiazomethane in 15 ml of dry benzene is added dropwise to a solution of 1.30 g (7.35 mmol) of 3-bromo-2-ketobutyric acid in 15 ml of dry benzene with vigorous stirring. Addition of the diazo compound is continued until a faint red color persisted (0.5 hr). The solvent is removed in vacuo and the yellow oil is dissolved in ether, filtered and concentrated to give 3.12 g crude benzhydryl ester. Chromatography on silica gel eluting with benzene affords 2.43 g (95%) pur benzhydryl 3-bromo-2-ketobutyrate as a yellow oil.

A solution of 1.6 g (8.85 mmol) of 3-bromo-2-ketobutyric acid and 7 g (4 equivalents) of O-t-butyl-N,N'-diisopropylpseudourea in 14 ml methylene chloride is stirred overnight at room temperature. After filtration, the solution is washed with $NaHCO_3$ and brine, dried and evaporated to an oil which is chromatographed on silica gel with benzene as eluant to give 1 g (45%) of t-butyl 3-bromo-2-ketobutyrate.

EXAMPLE 1

Methyl cis-1-(2,4-Dimethoxybenzyl)-3-azido-4-oxoazetidine-2-carboxylate

Method A

To a solution of 15.1 g (0.149 mole) of azidoacetic acid in 130 ml of anhydrous methylene chloride at 0° (ice bath) is added dropwise 21.0 ml (0.15 mole) of trifluoroacetic anhydride. This mixture is stirred at 0° for 15 minutes and then 20.8 ml (0.15 mole) of triethylamine is added dropwise. Stirring is continued for an additional 45 minutes and then the entire reaction mixture is transferred under argon into an additional funnel which is cooled externally by dry ice. The additional funnel is attached to a flask containing the imine from Preparation 1, anhydrous methylene chloride (200 ml), and triethylamine (20.8 ml, 0.15 mole). The solution of the mixed anhydride is added dropwise from the addition funnel to the solution of imine at 0°. Stirring is continued at 0° for 1 hour and then the dark reaction mixture is transferred to a separatory funnel and washed with $H_2O$, aqueous $NaHCO_3$ and brine and then dried over anhydrous magnesium sulfate. The solvents are removed in vacuo and the residue is chromatographed on 300 g of silica gel (70–230 mesh) affording an off white solid which is further purified by trituration with ether to give 14.45 g (45%) of the title product as a white solid; tlc: benzene:ethyl acetate (1:1), silica gel GF, Rf=0.64. Recrystallization from ethyl acetate-hexane affords an analytical sample, mp 82°–84°.

Method B

A solution of 1.6 g (9.55 mmol) dimethoxybenzylamine in 5 ml of $CH_2Cl_2$ is rapidly added at 0° to a solution of 1.06 g (10 mmol) freshly distilled methyl glyoxylate in 15 ml $CH_2Cl_2$. A slight exotherm occurred and water droplets appeared. Magnesium sulfate (5 g) is added and the mixture stirred at 0° for 2 hours. Fresh magnesium sulfate (1.0 g) is added, the magnesium sulfate removed by filtration under argon and washed with a minimum of $CH_2Cl_2$.

To a solution of 3.8 g (36 mmol) of azidoacetic acid (pumped in high vacuum 3 hr) in 125 ml of $CH_2Cl_2$ is added 10.6 ml (76 mmol) of triethylamine with cooling. Magnesium sulfate (3 gm) is added, the mixture stirred 10 min at room temperature, filtered under argon and washed with a 25 ml $CH_2Cl_2$.

The azidoacetic acid solution is added at 0° to the imine, sufficient methylene chloride is added to bring the total volume to 200 ml, the solution cooled to 0° under argon and 5.3 ml (38 mmol) trifluoroacetic anhydride added slowly over ½ hr with vigorous stirring and cooling. The mixture is stirred for 1 hr at 0°, allowed to warm to room temperature, transferred to a separatory funnel, washed with water, 5% $NaHCO_3$, 2% phosphoric acid and 5% $NaHCO_3$, dried over magnesium sulfate-charcoal; filtered and the filtrate is retreated twice with charcoal and evaporated to dryness. The residue is dissolved in a minimum of ether and stored at −20° to allow crystallization.

The crystalline mass was isolated and washed with cold ether to give 1.9 gm (64%) product, mp 79°–80.5°.

Method C

A solution of 1.6 g. of 2,4-dimethoxybenzylamine in 15 ml. of methylene chloride was shaken with an excess of magnesium sulfate then reacted with 1.05 g. of methyl glyoxylate in 2 ml. of methylene chloride at 25° C. (room temperature) overnight. The mixture was filtered, stripped and degassed with argon.

A solution of 1.5 g. of azidoacetic acid in 25 ml. of methylene chloride was cooled to 0° C. then reacted with 1.3 ml. of oxalyl chloride with 1.2 ml. of pyridine in 3 ml. of methylene chloride at 0° C. Argon was passed through the mixture which was stirred for one hour.

The imine from above was taken into 20 ml. of methylene chloride with 4.15 ml. of triethylamine. The solution of azidoacetyl chloride was added dropwise at 0° C. After one hour at 0° C. the mixture was washed with water, sodium bicarbonate solution, salt solution, dried and stripped. After passing over a silica gel column with methylene chloride the yield was 1.31 g. of the desired compound.

Substitution of ethyl glyoxylate, n-butyl, tert. butyl, benzyl or methoxybenzyl glyoxylate for methyl glyoxalate gives the corresponding ester congeners of the title compound.

EXAMPLE 2

Methyl cis-1-(2,4-Dimethoxybenzyl)-3-amino-4-oxoazetidine-2-carboxylate

A mixture containing 10.0 g (0.0312 mole) of methyl cis-1-(2,4-dimethoxybenzyl)-3-azido-4-oxoazetidine-2-carboxylate, 1.0 g of 10% palladium on carbon, and 200 ml of ethanol is hydrogenated for 2 hrs at 40°–45° and 60 psi of hydrogen. The reaction mixture is allowed to cool to 25° and is filtered through filter-aid. After removing the solvents in vacuo a clear, yellow gum of the title product is obtained.

EXAMPLE 3

Methyl cis-3-t-Butoxycarbonylamino-1-(2,4-dimethoxybenzyl)-4-oxoazetidine-2-carboxylate A solution of 5.5 g (18.8 mmole) of methyl cis-3-amino-1-(2,4-dimethoxybenzyl)-4-oxoazetidine-2-carboxylate in 100 ml of dry toluene is cooled to −78°; 2.5 ml (18.8 mmole) of triethylamine is added followed by rapid addition of 35 ml (42 mmole) of a 12% solution of phosgene in benzene. The mixture is stirred 15 min at −78°, 3 hr at −45° (acetonitrile-dry ice), then warmed to room temperature and concentrated to half volume in vacuum. To the resulting solution is added 50 ml of t-butanol and the mixture is stirred at room temperature overnight. The solvents are removed in vacuum, the residue is diluted with ethyl acetate and filtered. The filtrate is transferred to a separatory funnel and washed with 5% NaHCO$_3$, 5% HCl and brine; dried over magnesium sulfate and evaporated to dryness. Recrystallization of the crude, crystalline product affords 3.8 g (52%) of the title compound. Recrystallization from ether gives an analytical sample.

EXAMPLE 4

Methyl cis-1-(2,4-Dimethoxybenzyl)-3-phthalimido-4-oxoazetidine-2-carboxylate 2,4-Dimethoxybenzylamine (5.01 g, 0.03 mol) and methyl glyoxolate (3.17 g, 0.036 mol) are condensed as in Preparation 1 but at 0°–5° for 2 hours. The resulting imine is dissolved in methylene chloride (800 ml) and cooled in an ice bath. Triethylamine (5.4 ml) is added followed by the dropwise addition of a solution of N-phthalimido acetic acid chloride (7.54 g, 0.0338 mol) [*J. Amer. Chem. Soc.*, 71, 1856 (1949)] in methylene chloride (80 ml). After the reaction is stirred 2 hours, the solution is concentrated and then is washed with water, dilute HCl, and dilute NaHCO$_3$. The dried organic phase is evaporated to give the title product which is triturated with ether; 6.4 g (50%).

EXAMPLE 5

Methyl cis-1-(2,4-Dimethoxybenzyl)-3-(4,5-diphenyl-2-oxo-4-oxazolin-3-yl)-4-oxoazetidine-2-carboxylate The imine from Preparation 1 (1.43 g) is dissolved in dry methylene chloride (13 ml) and triethylamine (1 ml) and cooled in an ice bath. The acid chloride from Preparation 2 (2.0 g, 6.4 mmol) in methylene chloride (10 ml) is added over a 10-minute period. After one hour, the mixture is washed with water and 5% NaHCO$_3$, the dried solution is evaporated to a red oil which is chromatographed on 60 g of silica gel with 5% ethyl acetate in chloroform as eluant to give the title product, 2.37 g.

EXAMPLE 6

Methyl cis-1-(2,4-Dimethoxybenzyl)-3-phenoxyacetamido-4-oxo-2-azetidinecarboxylate The crude amine prepared in Example 2 from 10 g of the azido precursor is taken up in 100 ml of anhydrous methylene dichloride and is cooled to 0° in an ice bath. To this solution is added 4.32 ml (0.0312 mol) of triethylamine followed by the slow addition of a solution of 5.32 g (0.0312 mol) of phenoxyacetyl chloride in 40 ml of methylene dichloride. The mixture is stirred at 0° for 1 hr. then poured into a separatory funnel and extracted successively with water, aqueous HCl, aqueous NaHCO$_3$, brine and is dried over anhydrous magnesium sulfate. After filtration the solvent is removed in vacuo to give a yellow solid. This material is partially dissolved in ether, cooled to −25°, and filtered to afford 11.2 g (84%) of the title product as a white solid which is one spot on tlc: benzene-ethyl acetate (1:1), silica gel, Rf 0.38. An analytical sample, mp 115.5°–116.0°, is obtained by recrystallization from ethyl acetate-hexane.

EXAMPLE 7

When p-methoxybenzyl alcohol, isoborneol, benzyl alcohol, or 2,2,2-trichloroethanol is substituted for t-butanol in Example 3, methyl 3-(p-methoxybenzyloxycarbonylamino)-1-(2,4-dimethoxybenzyl)-4-oxoazetidine-2-carboxylate, methyl 3-(isobornyloxycarbonylamino)-1-(2,4-dimethoxybenzyl)-4-oxoazetidine-2-carboxylate, methyl 3-(benzyloxycarbonylamino)-1-(2,4-dimethoxybenzyl)-4-oxoazetidine-2-carboxylate, or methyl 3-(2,2,2-trichloroethoxycarbonylamino)-1-(2,4-dimethoxybenzyl)-4-oxoazetidine-2-carboxylate is obtained.

Methyl 3-(isobornyloxycarbonylamino)-1-(2,4-dimethoxybenzyl)-4-oxoazetidine-2-carboxylate can also be prepared by treating the 3-amino compound with isobornyloxycarbonyl chloride in the presence of base according to standard procedures; *Chem. Pharm. Bull.*, 20, 1017 (1972).

EXAMPLE 8

Methyl cis-3-t-Butoxycarbonylamino-4-oxoazetidine-2-carboxylate

A solution of 10.5 g (26.7 mmole) of methyl 3-t-butoxycarbonylamino-1-(2,4-dimethoxybenzyl)-4-oxoazetidine-2-carboxylate in 500 ml of acetonitrile is degassed with argon and warmed to 80°. A degassed solution of 15 g (55.5 mmole) of potassium persulfate and 7.5 g (28 mmole) of sodium monohydrogen phosphate in 150 ml of water is added in five portions over 1 hr. The reaction is stirred at 80°–85° under argon for 2–3 hrs until all starting material is consumed (tlc). The reaction mixture is cooled, concentrated in vacuum, shaken with ethyl acetate-water. The organic phase is washed with dilute HCl, NaHCO$_3$ solution and brine; dried over magnesium sulfate and evaporated to dryness. The residue is chromatographed over silica gel with 1:1 benzene-ethyl acetate to afford pure product which crystallized from ethyl acetate-hexane to yield 2.0 g (31%) of the title compound. A less pure fraction from the column, is crystallized from ethyl acetate-hexane to give an additional 0.5 g of product, overall yield, 38%.

EXAMPLE 9

When the products of Examples 1, 4, 5, 6 and 7 are treated with potassium persulfate and sodium monohydrogen phosphate according to the procedure of Example 8 the following products are obtained:

methyl cis-3-azido-4-oxoacetidine-2-carboxylate; 72% yield mp 77°–78° methyl cis-3-phthalimido-4-oxoazetidine-2-carboxylate; 40% yield methyl cis-3-(4,5-diphenyl-2-oxo-4-oxazolin-3-yl)-4-oxoazetidine-2-carboxylate, 32% yield methyl cis-3-phenoxyacetamido-4-oxoazetidine-2-carboxylate; 69% yield, mp 140°-41° methyl cis-3-isobornylcarbonylamino-4-oxoazetidine-2-carboxylate methyl cis-3-(p-methoxybenzyloxycarbonylamino)-4-oxoazetidine-2-carboxylate methyl cis-3-(benzyloxycarbonylamino)-4-oxoazetidine-2-carboxylate methyl cis-3-(2,2,2-trichloroethoxycarbonylamino)-4-oxoazetidine-2-carboxylate

EXAMPLE 10

Methyl cis-3-Amino-4-oxoazetidine-2-carboxylate

A solution of methyl cis-3-azido-4-oxoazetidine-2-carboxylate (8.5 g, 50 mmol) and an equivalent of p-toluenesulfonic acid in 200 ml of ethanol is hydrogenated for 3 hours over 1 g of 10% Pd on carbon at 40 psi. The solution is filtered and the filtrate is evaporated to title product or the tosylate salt which can be converted to the free base by standard methods.

EXAMPLE 11

A solution of anhydrous $K_2CO_3$ (249 mg, 1.8 mmol) in tetrahydrofuran (8 ml) and water (12 ml) is degassed with argon and then methyl cis-3-phenoxyacetamido-1-(2,4-dimethoxybenzyl)-4-oxoazetidine-2-carboxylate (150 mg, 0.35 mmol) is added. The reaction is stirred 1.5 hours at room temperature, the organic solvent is evaporated and the aqueous layer is acidified and extracted with methylene chloride. The dried extracts are evaporated to give a solid which is recrystallized from ethyl acetate-hexane to give pure cis-3-phenoxyacetamido-1-(2,4-dimethoxybenzyl)-4-oxoazetidine-2-carboxylic acid, mp 169°-170°(d).

Methyl cis-3-phenoxyacetamido-4-oxoazetidine-2-carboxylate is treated with $K_2CO_3$ in methanol-water as above to give cis-3-phenoxyacetamido-4-oxoazetidine-2-carboxylic acid, mp 150°-51° from ethyl acetate.

EXAMPLE 12 cis-3-t-Butoxycarbonylamino-2-hydroxymethyl-4-oxoazetidine

A solution of 2.0 g (8.2 mmole) of methyl 3-t-butoxycarbonylamino-4-oxoazetidine-2-carboxylate in 20 ml of tetrahydrofuran is cooled in ice and a solution of 0.75 g (20 mmole) of sodium borohydride in 10 ml of water is added. The mixture is stirred 20 min at 0° and then 1.5 hr at room temperature. Acetic acid is added drop-wise to decompose the excess borohydride and the mixture is concentrated in vacuum. The residue is diluted with brine and extracted with ethyl acetate. The organic phase is washed with brine and 5% $NaHCO_3$; dried over magnesium sulfate and evaporated to dryness to give 0.9 g (50%) of the title product as white crystals, mp 128°-131°.

EXAMPLE 13

When the 3-azido, 3-oxazolinyl, 3-phenoxyacetamido, 3-isobornyloxycarbonylamino, 3-(p-methoxybenzyloxycarbonylamino, and 3-benzyloxycarbonylamino compounds from Example 9 are reduced with sodium borohydride by the procedure of Example 12 the following products are obtained:

cis-3-azido-2-hydroxymethyl-4-oxoazetidine; 56% yield cis-2-hydroxymethyl-3-(4,5-diphenyl-2-oxo-4-oxazolin-3-yl)-4-oxoazetidine; ca. 100% yield cis-2-hydroxymethyl-3-phenoxyacetamido-4-oxoazetidine; 68% yield, mp. 153°-4° (from ethyl acetate)

cis-2-hydroxymethyl-3-isobornyloxycarbonyl-4-oxoazetidine cis-2-hydroxymethyl-3-(p-methoxybenzyloxycarbonylamino)-4-oxoazetidine cis-3-benzyloxycarbonylamino-2-hydroxymethyl-4-oxoazetidine

EXAMPLE 14 cis-3-t-Butoxycarbonylamino-4-oxo-2-azetidinylmethyl tosylate

To a solution of 0.9 g (4.3 mmole) of 98% p-toluenesulfonyl chloride in 10 ml of dry pyridine at 0° is added 0.9 g (4.15 mmole) of 3-t-butoxycarbonylamino-2-hydroxymethyl-4-oxoazetidine. The mixture is stirred for 2 hr at 0° and then stored at 5° overnight. After addition of 0.5 ml of 85% lactic acid, the mixture is stirred for 1 hr, poured into ethyl acetate and washed with dilute HCl, 5% $NaHCO_3$, and brine. The extract is dried over magnesium sulfate and evaporated to dryness to give 1.1 g (70%) of crystalline title product. Recrystallization from hexane-ethyl acetate gives an analytical sample, mp 160°-162° (d).

EXAMPLE 15

Treatment of the products obtained in Example 13 with p-toluenesulfonyl chloride according to the procedure of Example 14 gives the corresponding tosylates:

cis-3-azido-4-oxo-2-azetidinylmethyl tosylate; 80% yield mp 87°-89° cis-3-(4,5-diphenyl-2-oxo-4-oxazolin-3-yl)-4-oxo-2-azetidinylmethyl tosylate cis-3-phenoxyacetamido-4-oxo-2-azetidinylmethyl tosylate; 71% yield, mp 136° (d)

cis-3-isobornyloxycarbonylamino-4-oxo-2-azetidinylmethyl tosylate cis-3-(p-methoxybenzyloxycarbonylamino)-4-oxo-2-azetidinylmethyl tosylate cis-3-benzyloxy carbonylamino-4-oxo-2-azetidinylmethyl tosylate When cis-2-hydroxymethyl-1-(2,4-dimethoxybenzyl)-3-(4,5-diphenyl-2-oxo-4-oxazolin-3-yl)-4-oxoazetidine is reacted according to Example 13 except that mesyl chloride is substituted for p-toluenesulfonyl chloride, cis-3-(4,5-diphenyl-2-oxo-4-oxazolin-3-yl)-4-oxo-2-azetidinylmethyl mesylate is obtained; 73% yield, mp 185°-8° from ethyl acetate-hexane.

EXAMPLE 16 cis-3-Amino-4-oxo-2-azetidinylmethyl tosylate

A solution of cis-3-azido-4-oxo-2-azetidinylmethyl tosylate (5.0 g) in 50% aqueous acetic acid (50 ml) is cooled and then treated with zinc dust (2.0 g). The reaction is stirred for 30 minutes, filtered, and the solid washed with $H_2O$ (50 ml). The filtrate is saturated with $H_2S$ over ½ hour, the zinc sulfide is removed by filtration and the filtrate evaporated to near dryness. The residue is dissolved in ethyl acetate-water and adjusted to pH 10. Phases are separated and the aqueous layer is extracted with ethyl acetate. The dried organic phases are evaporated to give the amino compound; 3.0 g (66%).

EXAMPLE 17

A mixture of the 3-amino tosylate compound from Example 16 (0.14 g), N-t-butoxycarbonylphenylglycine (0.16 g) and dicyclohexylcarbodiimide (0.12 g) in methylene chloride (5 ml) is stirred one hour at 0° C. The solid is removed by filtration and the filtrate is evaporated to dryness. The residue is chromatographed on silica gel with 80:20 ethyl acetate-benzene as eluant to give cis-3-(α-t-butoxycarbonylaminophenylacetamido)-4-oxo-2-azetidinylmethyl tosylate; 0.19 g (70%).

2-Thienylacetic acid, the 3-amino derivative from Example 16, and dicyclohexylcarbodiimide (3.7 mmol of each) is reacted in methylene chloride as above. The mixture is diluted with ethyl acetate (150 ml) and filtered; the filtrate is washed with 5% NaHCO$_3$, dilute HCl, and brine, dried, evaporated and crystallized from acetone-ether to give cis-3-(2-thienylacetamido)-4-oxo-2-azetidinylmethyl tosylate; 0.9 g (69%) mp 121°–124°.

The 3-amino derivative is acylated with O-formylmandelic acid chloride in the presence of triethylamine to give cis-3-formylmandelamido-4-oxo-2-azetidinyl methyl tosylate, 98% mp 111°–113° (dec).

EXAMPLE 18 cis-3-Phenoxyacetamido-4-oxo-2-azetidinemethyl iodide

A mixture containing 13.68 g (33.9 mmol) of cis-3-phenoxyacetamido-4-oxo-2-acetidinemethyl tosylate, 39.8 g (0.265 mol) of sodium iodide and 550 ml of acetone is heated at reflux for a period of 6 hr and then is allowed to cool to ambient temperature. The acetone is removed in vacuo and the residue is suspended in ethyl acetate and extracted with water, sodium thiosulfate and brine. The dried ethyl acetate solution was evaporated in vacuo to give a yellow semi-crystalline residue. Recrystallization from ethyl acetate resulted in 10.3 g (84%) of crystalline product; mp 150° (dec).

EXAMPLE 19

When the appropriate tosylate or mesylate which are disclosed in Example 14, 15 and 17 is treated with sodium iodide by the procedure disclosed in Example 18 the following products are obtained:
cis-3-t-butoxycarbonylamino-4-oxo-2-azetidinylmethyl iodide
cis-3-azido-4-oxo-2-azetidinylmethyl iodide
cis-3-(4,5-diphenyl-2-oxo-4-oxazolin-3-yl)-4-oxo-2-azetidinylmethyl iodide
cis-3-(α-t-butoxycarbonylaminophenylacetamido)-4-oxo-2-azetidinylmethyl iodide, 78% yield
cis-3-thienylacetamido-4-oxo-2-azetidinylmethyl iodide, 98% yield
cis-3-formylmandelamido-4-oxo-2-azetidinylmethyl iodide
cis-3-isobornyloxycarbonylamino-4-oxo-2-azetidinylmethyl iodide
cis-3-(p-methoxybenzyloxycarbonylamino)-4-oxo-2-azetidinylmethyl iodide
cis-3-benzyloxycarbonylamino-4-oxo-2-azetidinylmethyl iodide

EXAMPLE 20

3-t-Butoxycarbonylamino-4-oxo-2-(p-methoxybenzylthiomethyl)-azetidine

To a solution of 1.1 g (2.97 mmole) of 3-N-t-butoxycarbonylamino-4-oxo-2-azetidinylmethyl tosylate in 15 ml of dry dimethylformamide under argon was added 4.0 g (26 mmole) of sodium iodide. The mixture was heated to 65° for 4 hours, then stirred at room temperature overnight. The resulting suspension was diluted with 50 ml of ethyl acetate, filtered, concentrated in vacuum, flushed with argon and 3.0 ml of p-methoxybenzyl mercaptan and 2.0 ml of triethylamine were added. The mixture was stirred at room temperature for 18 hours and then poured into ice water-ethyl acetate. The organic phase was separated and washed with water, 5% NaHCO$_3$ and brine; dried over magnesium sulfate and evaporated to dryness. The residue was chromatographed over silica gel with 1:1 benzene-ethyl acetate to afford after evaporation and crystallization from ethyl acetate-hexane, 335 mg (32%) of pure product, mp 120°–123°.

EXAMPLE 21

When an appropriate iodide derivative is reacted with p-methoxybenzyl mercaptan (2 equivalents) in the presence of triethylamine (2 equivalents) according to the procedure set forth in Example 20 the following compounds are obtained
cis-3-phenoxyacetamido-4-oxo-2-(p-methoxybenzylthiomethyl)azetidine; mp 139°–41°
cis-3-formylmandelamido-4-oxo-2-(p-methoxybenzylthiomethyl)azetidine
cis-3-(α-t-butoxycarbonylaminophenylacetamido)-4-oxo-2-(p-methoxybenzylthiomethyl)azetidine
cis-3-isobornylcarbonylamino-4-oxo-2-(p-methoxybenzylthiomethyl)azetidine
cis-3-(p-methoxybenzyloxycarbonylamino)-4-oxo-2-(p-methoxybenzylthiomethyl)azetidine
cis-3-benzyloxycarbonylamino-4-oxo-2-(p-methoxybenzylthiomethyl)azetidine

EXAMPLE 22 cis-3-(2-Thienylacetamido)-4-oxo-2-(triphenylmethylthiomethyl)azetidine

To a solution of 0.8 g (2.3 mmole) of cis-3-(2-thienylacetamido)-4-oxo-2-azetidinemethyl iodide and 0.9 g (9 mmole) of triethylamine in 10 ml of dry dimethylformamide is added 1.27 g (4.6 mmole) of triphenylmethanethiol. The mixture is stirred under argon overnight, diluted with 100 ml of ethyl acetate and washed with dilute HCl and water. After drying with magnesium sulfate, the extract is evaporated to dryness and the residue triturated with ether. The crystalline product is filtered and dried to give the title compound.

EXAMPLE 23

When the methyl iodide derivatives of Examples 18 and 19 are reacted with triphenylmethanethiol according to the procedure of Example 22 the following compounds are obtained.
cis-3-phenoxyacetamido-4-oxo-2-(triphenylmethylthiomethyl)azetidine
cis-3-t-butoxycarbonylamino-4-oxo-2-(triphenylmethylthiomethyl)azetidine
cis-3-(4,5-diphenyl-2-oxo-4-oxazolin-3-yl)-4-oxo-2-(triphenylmethylthiomethyl)azetidine
cis-3-(α-t-butoxycarbonylaminophenylacetamido)-4-oxo-2-(triphenylmethylthiomethyl)azetidine
cis-3-formylmandelamido-4-oxo-2-(triphenylmethylthiomethyl)azetidine
cis-3-isobornyloxycarbonylamino-4-oxo-2-(triphenylmethylthiomethyl)azetidine cis-3-(p-methoxybenzyloxycarbonylamino)-4-oxo-2-(triphenylmethylthiomethyl)azetidine
cis-3-benzyloxycarbonylamino-4-oxo-2-(triphenylmethylthiomethyl)azetidine

EXAMPLE 24

3-t-Butoxycarbonylamino-4-oxo-2-mercaptomethylazetidine

To a solution of 335 mg (0.95 mmole) of 3t-butoxycarbonylamino-4-oxo-2-(p-methoxybenzylthiomethyl-)azetidine in 5 ml of methanol and 20 ml of methylene chloride is added 1.7 g (5.3 mmole) of mercuric acetate. The mixture is stirred 24 hours under argon, diluted with excess ether and the precipitated mercury adduct filtered and washed well with ether. The mercury complex is suspended in water, layered with ethyl acetate and hydrogen sulfide gas is passed through the mixture for 1 hour. The mercuric sulfide is removed by filtration, the ethyl acetate layer is separated and washed with brine, dried over magnesium sulfate and evaporated to dryness. Trituration of the residue with 1:1 ethyl acetate-hexane gives 122 mg (55%) of the crystalline title product.

EXAMPLE 25 cis-3-(2-Thienylacetamido)-4-oxo-2-mercaptomethylazetidine

To a solution of 0.1 g (0.2 mmole) of cis-3-(2-thienylacetamido)-4-oxo-2-(triphenylmethylthiomethyl)-azetidine in 3 ml of methanol is added a solution containing 34 mg (0.2 mmole) of silver nitrate and 16 mg (0.2 mmole) of pyridine. A precipitate of the silver mercaptide is formed immediately. Hydrogen sulfide gas is passed through the mixture for 5 minutes, the silver sulfide removed by filtration and the filtrate diluted with ethyl acetate and washed with dilute HCl and brine. The extract is dried and evaporated to dryness; trituration with ether gives the title compound as white crystals.

EXAMPLE 26

When the p-methoxybenzylthiomethyl derivatives prepared in Example 21 are deblocked according to the procedure of Example 24 the following compounds are obtained.
cis-3-phenoxyacetamido-4-oxo-2-mercaptomethylazetidine
cis-3-formylmandelamido-4-oxo-2-mercaptomethylazetidine
cis-3-(α-t-butoxycarbonylaminophenylacetamido)-4-oxo-2-mercaptomethylazetidine
cis-3-isobornyloxycarbonylamino-4-oxo-2-mercaptomethylazetidine
cis-3-(p-methoxybenzyloxycarbonylamino)-4-oxo-2-mercaptomethylazetidine
cis-3-benzyloxycarbonylamino-4-oxo-2-mercaptomethylazetidin Similarly when the triphenylmethylthiomethyl derivatives prepared in Example 23 are deblocked by the procedure set forth in Example 25 the corresponding mercaptomethyl compounds are obtained.

EXAMPLE 27

A solution of methyl cis-3-(4,5-diphenyl-2-oxo-4-oxazolin-3-yl)-4-oxoazetidine-2-carboxylate (2.0 g, 3.9 mmol) in 50 ml ethanol is added to 10% Pd on carbon (0.5 g) which is premoistened with 2 ml 2 N HCl. The mixture is hydrogenated for 12 hours at 50 psi and 40°

C. After filtration, the solvent is removed and the oil is dissolved in methylene chloride which is then washed with NaHCO$_3$ and brine and dried. The solution is evaporated to give methyl cis-3-amino-1-(2,4-dimethoxybenzyl)-4-oxoazetidine-2-carboxylate.

EXAMPLE 28

Trichloroethyl 7β-t-Butoxycarbonylamino-6αH-2-hydroxy-8-oxo-4-thia-1-azabicyclo[4.2.0]octane-2-carboxylate To a suspension of 122 mg (0.52 mmole) of cis-3-t-butoxycarbonylamino-4-oxo-2-mercaptomethylazetidine in 20 ml of methylene chloride is added 156 mg (0.52 mmole) of trichloroethyl bromopyruvate followed at 0° by 50 μl of triethylamine. Methanol (5 ml) is added to effect solution and the mixture is stirred at room temperature for 1 hour. The solvents is removed in vacuum, the residue is dissolved in ethyl acetate which is washed with dilute HCl, 5% NaHCO$_3$ and brine; dried over magnesium sulfate and evaporated to dryness. The residue is chromatographed over silica gel with 1:2 ethyl acetate-benzene to afford 80 mg (35%) of the title product as a mixture of diastereomers.

EXAMPLE 29

Trichloroethyl 7β-amino-6αH-8-oxo-4-thia-1-azabicyclo-[4.2.0]oct-2-ene-2-carboxylate Method A To a solution of 70 mg (0.156 mmole) of the product from Example 28 in 3 ml of dry ethyl acetate is added 0.2 ml pyridine and 150 mg of methanesulfonyl anhydride. The mixture is stirred overnight at room temperature and then diluted with water. The aqueous solution is extracted with ethyl acetate and the extracts are washed with dilute HCl and 5% NaHCO$_3$ and then dried. Evaporation gives a residue which is chromatographed on silica gel with 80:20 benzene-ethyl acetate as eluant. The product (50 mg) is a mixture of the desired trichloroethyl cis-7-t-butoxycarbonylamino-8-oxo-4-thia-1-azabicyclo-[4.2.0]oct-2-ene-2-carboxylate and the 7-methylsulfonylamino derivative but separation before the following deblocking reaction is not necessary.

The above mixture is dissolved in 2 ml of methylene chloride, cooled to 0° and treated with 0.5 ml trifluoroacetic acid for 0.5 hr at 0°. The solution is washed with 5% NaHCO$_3$ and then extracted with dilute HCl. The aqueous phase is neutralized and extracted with ethyl acetate. The extracts are dried and then acidified with ethereal HCl. The hydrochloride salt of the title product is collected.

Method B

To a solution of the product from Example 28 (150 mg) in ethyl acetate (4 ml) is added pyridine (150 μl). The solution is cooled to −10° C., stirred 1 hour with thienyl chloride (50 μl), diluted with water, acidified and extracted with ethyl acetate. The extracts are washed with 5% NaHCO$_3$, and brine, dried and evaporated. The product is purified and deblocked as in Method A.

EXAMPLE 30

When cis-3-t-butoxycarbonylamino-4-oxo-2-mercaptomethylazetidine is condensed with benzhydryl bromopyruvate by the procedure of Example 28, benzhydryl 7β-t-butoxy-carbonylamino-6αH-2-hydroxy-8-oxo-4-thia-1-azabicyclo-[4.2.0]octane-2-carboxylate is obtained. Dehydration by either of the methods set forth in Example 29 gives benzhydryl 7β-t-butoxycarbonylamino-6αH-8-oxo-4-thia-1-azabicyclo[4.2.0]oct-2-ene-2-carboxylate.

Similarly as described above, use of t-butyl bromopyruvate gives the two compounds described above as their t-butyl ester.

EXAMPLE 31

7β-Amino-6αH-8-oxo-4-thia-1-azabicyclo[4.2.0]oct-2-ene-2-carboxylic acid

Method A

To a solution of 43 mg (0.1 mmole) of trichloroethyl cis-7-t-butoxycarbonylamino-8-oxo-4-thia-1-azabicyclo-[4.2.0]oct-2-ene-2-carboxylate in 6 ml of dimethylformamide and 6 ml of acetic acid is added over a 1.5 hr period 250 mg (3.8 mmole) zinc dust. The mixture is stirred vigorously for 3 hrs and then diluted with 50 ml of water. The mixture is acidified with dilute HCl, filtered and extracted with ethyl acetate. The organic phase is extracted with 5% NaHCO₃ which is acidified and reextracted into ethyl acetate. The final extracts are washed with brine, dried, and evaporated to give cis-7-t-butoxycarbonylamino-8-oxo-4-thia-1-azabicyclo[4.2.0]oct-2-ene-2-carboxylic acid.

The above product is dissolved in methylene chloride and treated with trifluoroacetic acid as outlined in Example 29. The reaction is evaporated in vacuo and the residue is triturated with ether to give the trifluoroacetate salt of the title product. The salt is dissolved in water and treated with basic ion-exchange resin ("Amberlite IR-45") until constant pH is obtained. After filtration, the aqueous solution is lyophilized to give the title product.

Method B

The ethyl acetate solution of trichloroethyl cis-7β-amino-6αH-8-oxo-4-thia-1-azabicyclo[4.2.0]oct-2-ene-2-carboxylate from Example 29 is treated with acetic acid and zinc dust as described above in Method A. After stirring 3 hrs, the reaction solution is acidified to pH 2 with dilute HCl, filtered, and evaporated to dryness. The residue is treated with basic ion-exchange as in Method A to give the title product.

Method C

A solution of benzhydryl 7β-t-butoxycarbonylamino-6αH-8-oxo-4-thia-1-azabicyclo[4.2.0]oct-2-ene-2-carboxylate (1 mmol) in methylene chloride is treated with trifluoroacetic acid at 0° as in Example 29, to cleave the two blocking groups and give the title compound.

EXAMPLE 32

Benzhydryl 7β-phenoxyacetamido-6αH-2-hydroxy-3-methyl-8-oxo-4-thia-1-azabicyclo[4.2.0]octane-2-carboxylate To a stirred solution of 0.234 g (0.88 mmol) of cis-3-phenoxyacetylamino-4-oxo-2-mercaptomethylazetidine and 0.304 g (0.88 mmol) benzhydryl 3-bromo-2-ketobutyrate in 26 ml of dry methylene chloride is added 122 μl (0.88 mmol) of triethylamine at room temperature under argon. The solution is stirred for 1 hr, then the methylene chloride is removed in vacuo and the residue dissolved in ethyl acetate. The ethyl acetate solution is washed with 3 N HCl solution, 5% NaHCO₃ solution and saturated NaCl solution. After drying, the solution is evaporated in vacuo to give 0.531 g of crude product. Chromatography of 0.466 g of crude product on silica gel eluting with ethyl acetate-hexane affords 320 mg of benzhydryl 7β-phenoxyacetamido-6αH-2-hydroxy-3-methyl-8-oxo-4-thia-1-azabicyclo[4.2.0]octane-2-carboxylate as a foam. (78%)

EXAMPLE 33

Benzhydryl 7β-phenoxyacetamido-6αH-3-methyl-8-oxo-4-thia-1-azabicyclo[4.2.0]oct-2-ene-2-carboxylate To a stirred solution of 0.200 g (0.39 mmol) of benzhydryl 7β-phenoxyacetamido-6αH-2-hydroxy-3-methyl-8-oxo-4-thia-1-azabicyclo[4.2.0]octane-2-carboxylate and 282 μl trifluoroacetic anhydride in 4 ml of dry ethyl acetate is added dropwise 161 μl (2.0 mmol) pyridine at 0° under argon. The solution is allowed to come to room temperature and stirred for 20 hours. The reaction mixture is diluted with ethyl acetate and washed twice with 5% NaHCO₃, 3 N HCl, and brine. The ethyl acetate layer is dried over MgSO₄ and concentrated in vacuo to afford 300 mg crude product. Chromatography on silica gel eluting with 50:50 ethyl acetate/benzene gives 21.8 mg (11%) of white, crystalline benzhydryl 7β-phenoxyacetamido-6αH-3-methyl-8-oxo-4-thia-1-azabicyclo[4.2.0]oct-2-ene-2-carboxylate and 42.1 mg (21%) of recovered starting material mp 155°–156°.

EXAMPLE 34

7β-Phenoxyacetamido-6αH-3-methyl-8-oxo-4-thia-1-azabicyclo-[4.2.0]oct-2-ene-2-carboxylic acid A solution of 0.062 g ($1.2 \times 10^{-4}$ mol) of benzhydryl 7β-phenoxyacetamido-6αH-3-methyl-8-oxo-4-thia-1-azabicyclo[4.2.0]oct-2-ene-2-carboxylate, 125 μl anisole, and 0.7 ml of trifluoroacetic acid in 2 ml of methylene chloride is stirred at 0° under argon for 1.3 hours. The trifluoroacetic acid and methylene chloride are removed in vacuo and the residue is treated with ethyl acetate and dilute HCl. The ethyl acetate is extracted with 5% NaHCO₃, and the aqueous combined extracts acidified to a pH of 1.5 and reextracted into ethyl acetate. The combined organic extracts are dried over MgSO₄, filtered and concentrated. After pumping under high vacuum, 25.2 mg of a yellow solid is isolated. Precipitation from methylene chloride-hexane solution afforded 18.7 mg (44%) of analytically pure title compound, mp 205°–15° (dec).

EXAMPLE 35 t-Butyl 7β-phenoxyacetamido-6αH-2-hydroxy-3-methyl-8-oxo-4-thia-1-azabicyclo[4.2.0]octane-2-carboxylate To a stirred solution of 0.083 g (0.31 mmol) of cis-3-phenoxyacetamido-4-oxo-2-mercaptomethylazetidine and 0.084 g (0.31 mmol) t-butyl 3-bromo-2-ketobutyrate in 10 ml of dry methylene chloride is added 44 μl (0.31 mmol) of triethylamine at room temperature under argon. The solution is stirred for 1.25 hours, the methylene chloride removed in vacuo, and the residue dissolved in ethyl acetate. The ethyl acetate is washed with 3 N HCl, 5% NaHCO₃ and brine. After drying, the solution is evaporated in vacuo to give 0.120 g of crude product. Chromatography on silica gel eluting with 50:50 ethyl acetate-hexane gives 93.8 mg (70%) of a colorless oil. After standing at room temperature, the oil solidified to give crystalline title compound, mp 138°–150°.

EXAMPLE 36 t-Butyl 7β-phenoxyacetamido-6αH-3-methyl-8-oxo-4-thia-1-azabicyclo[4.2.0]oct-2-ene-2-carboxylate To a stirred solution of 0.302 g (0.72 mmol) of the 2-hydroxy compound from Example 35 and 200 μl (1.43 mmol) of trifluoroacetic anhydride in 6 ml dry ethyl acetate is added dropwise 290 μl (3.58 mmol) of pyridine at 0° under argon. The solution is allowed to come to room temperature and stir overnight (20 hrs). The reaction mixture is diluted with ethyl acetate and washed with 5% NaHCO$_3$, 3 N HCl and brine. The ethyl acetate solution is dried over MgSO$_4$ and concentrated. Chromatography on silica gel eluting with ethyl acetate-hexane mixture affords 49.5 mg (17%) of the title compound as a yellow solid, mp 147°-149°.

EXAMPLE 37

Substitution of cis-3-t-butoxycarbonylamino-4-oxo-2-mercaptomethylazetidine for the phenoxyacetamido derivative in the procedures of Examples 33 and 35 gives the benzhydryl and t-butyl esters of 7β-t-butoxycarbonylamino-6αH-2-hydroxy-3-methyl-8-oxo-4-thia-1-azabicyclo-[4.2.0]octane-2-carboxylic acid.

The above esters are each treated with trifluoroacetic anhydride by the procedure in Examples 33 and 36 or with the other dehydrating agents set forth in Example 29 to give benzhydryl and t-butyl 7β-t-butoxycarbonylamino-6αH-3-methyl-8-oxo-4-thia-1-azabicyclo[4.2.0]oct-2-ene-2-carboxylate.

Treatment of either of the above esters with trifluoroacetic acid by the procedure in Example 34 gives 7β-amino-6αH-3-methyl-8-oxo-4-thia-1-azabicyclo[4.2.0]oct-2-ene-2-carboxylic acid.

EXAMPLE 38 t-Butyl 7β-Phenoxyacetamido-6αH-3-bromomethyl-8-oxo-4-thia-1-azabicyclo[4.2.0]oct-2-ene-2-carboxylate A suspension of 30.0 mg (0.075 mmol) of t-butyl cis-7β-phenoxyacetamido-6αH-3-methyl-8-oxo-4-thia-1-azabicyclo[4.2.0]oct-2-ene-2-carboxylate and 28 mg (0.15 mmol) of N-bromosuccinimide in 5 ml of carbon tetrachloride is degassed, a trace of azobisisobutyronitrile is added and the mixture refluxed for 2 hrs. After cooling, the mixture is filtered, evaporated to dryness, redissolved in ethyl acetate, washed with 5% sodium bisulfite, dried over magnesium sulfate and evaporated to dryness. The residue was chromatographed on silica gel with 5% ethyl acetate in chloroform to give on trituration with methylene chloride-hexane, 10.8 mg of the title compound as a pale yellow amorphous solid.

EXAMPLE 39

7β-Phenoxyacetamido-6αH-3-acetoxymethyl-8-oxo-4-thia-1-azabicyclo[4.2.0]oct-2-ene-2-carboxylic acid A mixture of 48 mg (0.1 mmole) of the bromomethyl derivative from Example 38 and 200 mg of silver acetate in 10 ml of acetone is stirred at room temperature for 1 day. The mixture is filtered, the filtrate is evaporated to dryness and chromatographed over silica gel with 5% ethyl acetate in chloroform to afford the t-butyl ester of the title compound.

The above material is dissolved in ice cold trifluoroacetic acid containing 10% anisole. The solution is stirred at 0° for ½ hr, the solvent is removed in vacuum, the residue is dissolved in ethyl acetate and extracted with 5% sodium bicarbonate solution. The aqueous extract is carefully acidified and extracted with ethyl acetate, the extract is dried over magnesium sulfate and evaporation to dryness. Trituration with hexane affords the title compound.

EXAMPLE 40

When the t-butyl 7β-t-butoxycarbonylamino-6αH-3-methyl-8-oxo-4-thia-1-azabicyclo[4.2.0]oct-2-ene-2-carboxylate is treated with N-bromosuccinimide by the procedure of Example 38, t-butyl 7β-t-butoxycarbonylamino-6αH-3-bromomethyl-8-oxo-4-thia-1-azabicyclo[4.2.0]oct-2-ene-2-carboxylate is obtained.

Treatment of the above bromomethyl derivative with sodium acetate or silver acetate according to the procedure of Example 39 gives t-butyl 7β-t-butoxycarbonylamino-6αH-3-acetoxymethyl-8-oxo-4-thia-1-azabicyclo-[4.2.0]oct-2-ene-2-carboxylate When the above compound is treated with trifluoroacetic acid by the procedure of Example 39, 7β-amino-6αH-3-acetoxymethyl-8-oxo-4-thia-1-azabicyclo[4.2.0]oct-2-ene-2-carboxylic acid is obtained.

EXAMPLE 41

Trichloroethyl 7β-Phenoxyacetamido-6αH-2-hydroxy-8-oxo-4-thia-1-azabicyclo[4.2.0]octane-2-carboxylate To a solution of 273 mg (1.02 mmol) of cis-3-phenoxyacetamido-4-oxo-2-mercaptomethylazetidine and 305 mg (1.02 mmol) of trichloroethyl bromopyruvate in 30 ml of methylene chloride is added slowly at 0°, 0.110 ml triethylamine. After stirring for two hours at room temperature, the mixture is evaporated to dryness, the residue is dissolved in ethyl acetate, washed with 5% HCl, 5% NaHCO$_3$, and saturated NaCl, evaporated to dryness and chromatographed over silica gel with 1:1 ethyl acetate-hexane as eluant to give the title product, 256 mg (52%).

EXAMPLE 42

7β-Phenoxyacetamido-6αH-8-oxo-4-thia-1-azabicyclo[4.2.0]oct-2-ene-4-carboxylic acid To a cooled solution (0° C.) of 0.477 g (1 mmol) of trichloroethyl 7β-phenoxyacetamido-6αH-2-hydroxy-8-oxo-4-thia-1-azabicyclo[4.2.0]octane-2-carboxylate in 10 ml ethyl acetate is added 65 μl of trifluoroacetic anhydride and then 362 μl of pyridine. The reaction is stirred overnight at room temperature and then diluted with ethyl acetate. The solution is washed with NaHCO$_3$ solution, 3 N NCl and saturated saline solution. The dried solution is evaporated to give the ester of the title product which is recrystallized from benzene; 157 mg (34%).

In 24 ml solution of dimethylformamide-glacial acetic acid (1:1) is dissolved 70 mg of the above ester. To this solution is added over a 1.5 hour period 500 mg of zinc dust which has been treated with 5% HCl for 3 minutes, washed with water, ethanol, and ether and then dried. The reaction mixture is stirred 3 hours at room temperature, diluted with water, acidified with 3 N HCl and extracted with ethyl acetate. The extracts are washed with a large volume of 5% NaHCO$_3$. The aqueous solution is acidified to pH 2 with HCl and extracted with ethyl acetate. The dried extracts are concentrated in vacuo and then high vacuum is used to remove residual acetic acid. The residue is triturated with ether-hexane, dissolved in methylene chloride and precipitated with hexane to give the title product, mp 194°–5°(dec).

EXAMPLE 43

7β-(α-Aminophenylacetamido)-6αH-8-oxo-4-thia-1-azabicyclo-[4.2.0]oct-2-ene-2-carboxylic acid Benzhydryl bromopyruvate (500 mg) was dissolved in benzene (8 ml) and tetrahydrofuran (1 ml), cooled to 10° C. and treated with a solution of diphenyldiazomethane (286 mg) in benzene (10 ml). The solution is stirred until colorless and then evaporated to dryness. The residue is dissolved in methylene chloride (5 ml) and cooled to 0° C. and then cis-3-(α-t-butoxycarbonylaminophenylacetamido)-4-oxo-2-mercaptomethylazetidine (465 mg) is added. The reaction is stirred for one hour and evaporated to dryness to give a residue which dissolved in ethyl acetate-water. The ethyl acetate phase is washed with 1% HCl, NaHCO₃ solution and NaCl solution. The dried organic phase is evaporated to give benzhydryl 7-(α-t-butoxycarbonylaminophenylacetamido)-2-hydroxy-8-oxo-4-thia-1-azabicyclo[4.2.0]octane-2-carboxylate.

To a solution of the above product (200 mg) in ethyl acetate (4 ml) is added pyridine (150 μl). The solution is cooled to −10° C., stirred one hour with thionyl chloride (50 μl), diluted with water, acidified and extracted with ethyl acetate. The extracts are washed with 5% NaHCO₃ and NaCl solution, dried and evaporated. The residue is chromatographed over silica gel with 5:1 benzene-ethyl acetate as eluant to give the blocked derivative of the title product (50 mg).

The blocking groups are removed by stirring a solution of the above product (118 mg) in methylene chloride (10 ml), anisole (0.2 ml) and trifluoroacetic acid (2.0 ml) for 45 minutes at 0° C. under argon. The reaction is allowed to warm to room temperature and then is evaporated to dryness under high vacuum. The trifluoroacetate salt of the title compound is triturated with ether and reprecipitated from methanol-ether.

EXAMPLE 44

7β-(α-Amino-p-hydroxyphenylacetamido)-6αH-8-oxo-4-thia-1-azabicyclo[4.2.0]oct-2-ene-2-carboxylic acid To a solution of 265 mg (1 mmol) of N-t-butoxycarbonyl-p-hydroxyphenylglycine in dry tetrahydrofuran (10 ml) is added triethylamine (0.14 ml). After cooling to −10°, isobutyl chloroformate (1 mmol) in 2 ml of tetrahydrofuran is added dropwise and the reaction is stirred 20 minutes. A mixture of 270 mg (1 mmol) of cis-3-amino-4-oxo-2-azetidinemethyl tosylate and 0.14 ml of triethylamine in 50% aqueous tetrahydrofuran (5 ml) is cooled to −10° and added to the reaction solution. The resulting solution is stirred one hour at low temperature and then allowed to warm to room temperature. The organic solvent is removed and the aqueous residue is diluted with water and extracted with ethyl acetate. The aqueous solution is layered with ethyl acetate, cooled and acidified. Phases are separated and the aqueous layer is extracted with ethyl acetate. The dried organic layers are evaporated to give the cis-3-(α-t-butoxycarbonylamino-p-hydroxyphenylacetamido)-4-oxo-2-azetidinylmethyl tosylate.

The above tosylate is reacted with NaI followed by p-methoxybenzyl mercaptan according to the procedure of Example 20 to give the p-methoxybenzylthio derivative which is cleaved by the procedure of Example 24 to give cis-3-(α-t-butoxycarbonylamino-p-hydroxyphenylacetamido)-4-oxo-2-mercaptomethylazetidine.

The above product is reacted with benzhydryl bromopyruvate according to the procedure of Example 43 and the subsequent reaction sequence disclosed therein is continued to give the title product.

EXAMPLE 45

7β-(2-Thienylacetamido)-6αH-8-oxo-4-thia-1-azabicyclo-[4.2.0]oct-2-ene-2-carboxylic acid The dry ethyl acetate solution from Example 29 of trichloroethyl 7β-amino-6αH-8-oxo-4-thia-1-azabicyclo-[4.2.0]oct-2-ene-2-carboxylate which is obtained from 0.012 g of the t-butoxycarbonyl derivative is treated with 0.2 ml 2-thienylacetyl chloride and 0.2 ml of triethylamine. The reaction is stirred 2 hours at room temperature and then diluted with NaHCO₃ solution. The organic layer is separated, washed with 3 N HCl, dried, and evaporated to give the 7-thienylacetamido derivative.

The above ester is treated with zinc dust and acetic acid according to the procedure in Example 42 to give the title product.

EXAMPLE 46

7β-Phenoxyacetamido-6αH-8-oxo-4-thia-1-azabicyclo[4.2.0]-oct-2-ene-2-carboxylic acid The dry ethyl acetate solution of trichloroethyl 7β-amino-6αH-8-oxo-4-thia-1-azabicyclo[4.2.0]oct-2-ene-2-carboxylate from Example 29 is cooled to 0° and treated with one equivalent each of phenoxyacetyl chloride and triethylamine. After stirring one hour, the mixture is washed with dilute HCl and brine. The organic phase is dried and evaporated to give trichloroethyl ester of the title product.

The trichloroethyl ester was treated with zinc dust and acetic acid by the procedure given in Example 42 to give the title product.

EXAMPLE 47

7β-Methylsulfonylacetamido-6αH-8-oxo-4-thia-1-azabicyclo-[4.2.0]oct-2-ene-2-carboxylic acid A solution of 200 mg (1 mmol) of trichloroethyl 7β-amino-6αH-8-oxo-4-thia-1-azabicyclo[4.2.0]oct-2-ene-2-carboxylate and 0.14 ml triethylamine in 10 ml of dimethylformamide is stirred with 236 mg (1 mmol) of the N-hydroxysuccinimide ester of methylsulfonylacetic acid for two hours at room temperature. The reaction is poured into ice water and the resultant solution is extracted with ethyl acetate. The aqueous phase is acidified to pH 2 and extracted with ethyl acetate. The dried extracts are evaporated to give the ester which is deblocked as in Example 42 to give the title product.

EXAMPLE 48

When trichloroethyl 7β-amino-6αH-8-oxo-4-thia-1-azabicyclo[4.2.0]oct-2-ene-2-carboxylic acid is acylated with one of the following carboxylic acids:
α-formyloxyphenylacetic acid
trifluoromethylmercaptoacetic acid
methylmercaptoacetic acid
2,2,2-trifluoroethylsulfinylacetic acid
cyanoacetic acid
cyanomethylmercaptoacetic acid
cyanomethylsulfinylacetic acid
cyanomethylsulfonylacetic acid α-carboxy-2-thienylacetic acid
α-carboxy-3-thienylacetic acid
α-sulphophenylacetic acid
3-thienylacetic acid
1-tetrazolylacetic acid
using the acid or an activated derivative thereof, all of which are known in the art, and which have any sensitive or interfering group suitably protected, according to known acylation procedures such as those set forth in Examples 43, 44, 45 or 47 followed by removal of all protecting groups by standard methods, gives the corresponding 7β-acylamino-6αH-8-oxo-4-thia-1-azabicyclo[4.2.0]oct-2-ene-2-carboxylic acid.

EXAMPLE 49

When α-(N-t-butoxycarbonylamino)-4-hydroxy-3-fluorophenylacetic acid or α-(N-t-butoxycarbonylamino)-4-(t-butoxycarbonylmethylamino)-phenylacetic acid is substituted for N-t-butoxycarbonyl-p-hydroxyphenylglycine in Example 44, the following compounds are obtained:

7β-(α-amino-4-hydroxy-3-fluorophenylacetamido)-6αH-8-oxo-4-thia-1-azabicyclo[4.2.0]oct-2-ene-2-carboxylic acid 7β-(α-amino-4-carboxymethylaminophenylacetamido)-6αH-8-oxo-4-thia-1-azabicyclo[4.2.0]oct-2-ene-2-carboxylic acid.

EXAMPLE 50

7β-(α-Carboxyphenylacetamido)-6αH-8-oxo-4-thia-1-azabicyclo[4.2.0]oct-2-ene-2-carboxylic acid Equimolar quantities of the N-hydroxysuccinimidyl ester of α-t-butoxycarbonylphenylacetic acid, cis-3-amino-4-oxo-2-azetidinemethyl tosylate and triethylamine are stirred together in dimethylformamide for two hours at room temperature. The reaction is poured into ice water and the aqueous solution is washed with ethyl acetate, acidified to pH 2 and extracted with ethyl acetate. The dried extracts are evaporated to give the cis-3-(α-t-butoxycarbonylphenylacetamido)-4-oxo-2-azetidinylmethyl tosylate.

When the above tosylate is substituted for the tosylate in Example 44 and the reaction sequence disclosed therein is continued, the title product is obtained.

EXAMPLE 51

When 7β-amino-6αH-3-methyl-8-oxo-4-thia-1-azabicyclo[4.2.0]oct-2-ene-2-carboxylic acid is acylated with 2-thienylacetic acid, phenoxyacetic acid, methylsulfonylacetic acid, α-formyloxyphenylacetic acid, trifluoromethylmercaptoacetic acid, 2,2,2-trifluoroethylsulfinylacetic acid, cyanoacetic acid, cyanomethylmercaptoacetic acid, cyanomethylsulfinylacetic acid, cyanomethylsulfonylacetic acid, α-carboxy-2-thienylacetic acid, α-carboxy-3-thienylacetic acid, α-sulphophenylacetic acid, 3-thienylacetic acid, 1-tetrazolylacetic acid, α-aminophenylacetic acid, α-amino-p-hydroxyphenylacetic acid, α-amino-4-hydroxy-3-fluorophenylacetic acid, α-amino-p-carboxymethylaminophenylacetic acid, or α-carboxyphenylacetic acid, using the acid itself or an activated derivative thereof all of which are known in the art and which have any sensitive or interferring groups suitably protected, according to known acylation procedures such as those set forth in Examples 43, 44, 45 or 47 followed by removal of all protecting groups by standard methods, the corresponding 7β-acylamino-6αH-3-methyl-8-oxo-4-thia-1-azabicyclo[4.2.0]oct-2-ene-2-carboxylic acid is obtained.

EXAMPLE 52

When 7β-amino-6αH-3-acetoxymethyl-8-oxo-4-thia-1-azabicyclo[4.2.0]oct-2-ene-2-carboxylic acid is acylated with 2-thienylacetic acid, phenoxyacetic acid, methylsulfonylacetic acid, α-formyloxyphenylacetic acid, trifluoromethylmercaptoacetic acid, 2,2,2-trifluoroethylsulfinylacetic acid, cyanoacetic acid, cyanomethylmercaptoacetic acid, cyanomethylsulfinylacetic acid, cyanomethylsulfonylacetic acid, α-carboxy-2-thienylacetic acid, α-carboxy-3-thienylacetic acid, α-sulphophenylacetic acid, 3-thienylacetic acid, 1-tetrazolylacetic acid, α-aminophenylacetic acid, α-amino-p-hydroxyphenylacetic acid, α-amino-4-hydroxy-3-fluorophenylacetic acid, α-amino-p-carboxymethylaminophenylacetic acid, or α-carboxyphenylacetic acid, using the acid itself or an activated derivative thereof all of which are known in the art and which have any sensitive or interfering groups suitably protected, according to known acylation procedures such as those set forth in Examples 43, 44, 45 or 47 followed by removal of all protecting groups by standard methods, the corresponding 7β-acylamino-6αH-3-acetoxymethyl-8-oxo-4-thia-1-azabicyclo[4.2.0]oct-2-ene-2-carboxylic acid is obtained.

EXAMPLE 53

Methyl cis-3-amino-1-(2,4-dimethoxyphenyl-4-oxoazetidine-2-carboxylate

The lactam product from Example 4 (8.0 g) was cooled in a dry-ice-acetone bath under nitrogen then 1.1 g of methylhydrazine added. After stirring for 20 minutes the mixture was re-cooled to −78° C. and 4.5 ml of the hydrazine added. The volatiles were removed at the pump to give 8.3 g of half opened hydrazide intermediate. This compound (3.5 g) in 50 ml of chloroform was heated on the steam bath for 30 minutes then allowed to stand several days. The liquid was evaporated to give a yellow oil of mostly cis-3-amino compound which may be optionally purified over a silica gel column using chloroform-isopropanol.

The yellow oil in 25 ml of methylene chloride cooled to 0° C. was reacted with 1.3 g of phenoxyacetyl chloride and 1 ml of triethylamine to give the 3-phenoxyacetamido derivative, m.p. 114.5°–115.5° C.

EXAMPLE 54

A. n-Butyl cis-1-benzhydryl-3-azido-4-oxo-2-azetidine carboxylate (2)

To a mixture containing 4.16 g (22.7 mmole) of benzhydrylamine and anhydrous magnesium sulfate in 50 ml of dichloromethane at 25° C. was added a solution of 2.96 g (22.7 mmole) of n-butyl glyoxylate in 50 ml of dichloromethane. The reaction mixture was stirred at room temperature overnight and then was filtered and the solvents were removed in vacuo to afford the imine.

To a solution of 2.29 g (22.7 mmole) of azidoacetic acid in 100 ml of anhydrous dichloromethane at 0° C. under an argon atmosphere was added dropwise 3.1 ml (22.7 mmole) of trifluoroacetic anhydride. The solution was stirred at 0° C. for 10 min then 3.15 ml (22.7 mmole) of triethylamine was added dropwise and stirring was continued at 0° C. for an additional 20 min. To this light-yellow solution at 0° C. undr argon was added a solution of the imine generated above (theo. 22.7 mmole) and 3.15 ml (22.7 mmole) of triethylamine in 50 ml of dichloromethane. The reaction mixture was stirred at 0° C. for 1 hour and then was stirred at ambient temperature overnight.

The resulting dark brown reaction mixture was extracted once with water, three times with dilute aqueous hydrochloric acid and twice with aqueous sodium bicarbonate. The dichloromethane extracts were combined and dried over anhydrous magnesium sulfate and the solvents were removed in vacuo to afford 6.3 g of dark brown oil. This material was chromatographed on a column of 130 g of Silica Gel (70–230 Mesh) and the desired β-lactam was removed with 50% ethylacetate-benzene to afford 1.68 g (19.5%) as a yellow solid. Recrystallization of this material from hexanethylacetate resulted in a white crystalline solid with m.p. 101.5°–102.5° C.

B. Butyl cis-3-azido-4-oxo-2-azetidinecarboxylate (3)

A mixture of 200 mg (0.529 mmole) of butyl cis-1-benzhydryl-3-azido-4-oxo-2-azetidine carboxylate, 473 mg (1.75 mmole) of potassium persulfate, 307 mg (0.858 mmole) of disodium phosphate dodecahydrate, 9.2 ml of water and 8.4 ml of acetonitrile was thoroughly degassed with argon and then heated to 80°–85° C. under argon for three hours. The reaction mixture was cooled and the acetonitrile removed on the rotary evaporator. The aqueous residue was saturated with solid sodium chloride and extracted three times with ethyl acetate. The combined organic extractions were washed with brine, dried over anhydrous sodium sulfate, filtered, and concentrated in vacuo to give 197 mg of crude material. This material was chromatographed on ten grams of 70–230 mesh silica gel and 31 mg (28%) of the desired product, a light yellow foam was eluted with 20% EtOAc in benzene. tlc: silica gel GF; 20% ethylacetate benzene, R.f.=0.15.

Various methoxy substituted benzhydrylamines can be substituted in these reactions such as 4-methoxybenzhydrylamine, 4,4'-dimethoxybenzhydrylamine, 2,3-dimethoxybenzhydrylamine, 2,2',4,4'-tetramethoxybenzhydrylamine. Also equimolar quantities of other glyoxalates may be used such as benzyl glyoxalate, isoamyl glyoxalate, hexyl glyoxalate, trichloroethyl glyoxalate or p-methoxybenzyl glyoxalate.

EXAMPLE 55

The "protected" and "acyl" glycines, their acid chlorides and mixed anhydrides are prepared and used employing methods known to the art, for example in Greenstein and Winitz, Chemistry of the Amino Acids, Volume 2, pages 924–945, 965–982 or E. H. Flynn, Cephalosporins and Penicillins, Chapter 16, Academic Press (1972), or P. G. Sammes, Chem. Rev. 76, 113 (1976).

Substituting molar equivalents of the following acylating agents in the methods detailed in Examples 1, 4 or 5 gives the azetidinones of Formula 3a in which alk is methyl.

| Acylating agent | 3a when A is: |
|---|---|
| N-(t.-butoxycarbonyl)-glycyl chloride | t.-butoxycarbonylamino |
| N-(trichloroethoxycarbonyl)-glycyl chloride | trichloroethoxycarbonyl-amino |
| N-(carbobenzoxy)-glycyl isobutylcarbonate | benzyloxycarbonylamino |
| phenoxyacetamidoacetyl chloride | phenoxyacetamido |
| O-benzylmandeloylglycyl chloride | O-benzylmandeloylamino |
| D-α-t.-butoxycarboxamido-phenylacetamidoacetyl-trifluoroacetic anhydride | D-α-t.-butoxycarboxamido-pheylacetamido |
| O-formylmandeloylglycyl chloride | Oformylmandeloylamino |
| 2,6-dimethoxybenzoylglycyl chloride | 2,6-dimethoxybenzoylamino |
| p-nitrobenzoylglycyl bromide | p-nitrobenzoylamino |
| N-tritylglycyl chloride | tritylamino |
| N-(iso-bornyloxycarbonyl)-glycyl chloride | isobornyloxycarbonylamino |
| N-(p-methoxybenzylcarbonyl-glycyl chloride | p-methoxybenzylcarbonyl-amino |
| cyanoacetamidoacetyl chloride | cyanoacetamido |
| methyl-1-tetrazolylacetamidoacetyl chloride | methyl-1-tetrazolylacetamido |
| N-succinimidoacetamidoacetyl acetyl cloride | succinimidoacetamido |
| N-maleimidoacetamidoacetyl chloride | maleimidoacetamido |

EXAMPLE 56

Substituting molar equivalents of each end product described in Example 55 into the persulfate procedure of Example 6 using reaction temperatures from −75° to 0° C. gives the corresponding debenzylated azetidinone.

EXAMPLE 57

The product of Example 10, methyl cis-3-amino-4-oxoacetidine-2-carboxylate, is acylated using either the mixed anhydride procedures known in the cephalosporin-penicillin art such as those referred to in the Flynn reference of Example 54 (page 677) or the reaction with a substituted acetyl chloride (page 666). This sequence of reactions is preferred to that of Example 54, that is for monovalent amine groups which are formed with great difficulty or for thio-containing acylamino compounds which are not susceptible to hydroxyl radical supplying oxidation agents. α-Thienylacetyl chloride gives methyl cis-3-α-thienylacetamido-4-oxoacetidine-2-carboxylate; 4-pyridylthioacetyl chloride in dimethylformamide with triethylamine gives methyl cis-3-α-(4-pyridylthio)acetamido-4-oxoazetidine-2-carboxylate; trifluoroethylsulfinylacetyl chloride gives methyl cis-3-2,2,2-trifluoroethylsulfinylacetamido-4-oxoazetidine-2-carboxylate; O-formyl-D-mandeloyl chloride gives methyl cis-3-D-mandeloylamino-4-oxoazetidine-2-carboxylate, O-formyl ester; t.-boc of D-p-hydroxyglycine anhydride with trichloroethyl chloroformate gives after reaction and removal of the t.-boc protecting group with trifluoroacetic acid methyl cis-3-D-p-hydroxyglycylamino-4-oxoazetidine-2-carboxylate.

Each of these intermediates are reacted further in Scheme I, compound 5 to 8 and 9.

EXAMPLE 58

Substituting p-methoxybenzylamine in the cyclization reaction described above gave 4-carbomethoxy-3-phthalimido-1-(p-methoxybenzyl)azetidin-2-one, m.p. 141°–142°.

A solution of 2.45 g (6.22 mmol) of the azetidinone in 250 ml of acetonitrile and 75 ml of water was degassed with argon. At 80°, a degassed solution of 23.5 g (87.2 mmol) of potassium persulfate and 7.77 g (55 mmol) of disodium phosphate was added in 6 portions over 1 hour. The mixture was cooled, the acetonitrile removed in vacuum, the aqueous residue saturated with sodium chloride and extracted with warm (40°) hexane (3 × 100 ml) then with ethyl acetate (5 × 125 ml). The ethyl acetate extract was washed with sodium bicarbonate, brine, dried and evaporated to dryness. Titration with ether gave 4-carbomethoxy-3-phthalimido-azetidin-2-one, m.p. 124°–6°.

The deblocking of the ring nitrogen atom using persulfate gives excellent yields and is not dependent of the 2 or 3 substituents which are inert to persulfate. For example, the reaction has been run with aromatic alkyl or acyl groups at position 2 to give good yields. Most commonly the 1-benzyl blocked acetidinone is reacted with 14 molar equivalents of potassium persulfate, 9 molar equivalents of disodium phosphate in aqueous acetonitrile at elevated temperatures such as at reflux for ½ to 1½ hours.

EXAMPLE 59

As an example of the utility of the end products prepared according to this invention, following is the in vitro spectrum of the compound of Example 45, 7β-(2-thienylacetamido)-6αH-8-thia-1-azabicyclo[4.2.0]-oct-2-ene-2-carboxylic acid along with the spectra of three commercially useful anti-bacterial agents. Based on such comparative data to evaluate efficacy and potency the end products prepared as described herein may be used as topical or systemic anti-bacterial agents in the same manner as the prior art cephalosporins or penicillins.

TABLE I

| | 1 Staph. aureus HH 127 | 2 Staph. aureus SK & F 23390 | 3 Staph. aureus Villatuz (M.R.) SK & F 70399 | 4 Staph. faecalis HH 34358 | 5 E. coli SK & F 12140 | 6 E. coli HH 33779 | 7 Kleb. pneumoniae SK & F 4200 | 8 Kleb. pneumoniae SK & F 1200 |
|---|---|---|---|---|---|---|---|---|
| Pen G. | 6.3 | 0.1 | 200 | 0.8 | 6.3 | 12.5 | 1.0 | 12.5 |
| Cephalothin | 0.2 | 0.1 | 25 | 12.5 | 1.6 | 3.1 | 0.8 | 0.8 |
| Cefazolin | 0.2 | 0.2 | 100 | 3.1 | 0.8 | 0.8 | 0.8 | 0.4 |
| Ex.45 | 25 | 12.5 | >200 | >200 | 12.5 | 25 | 6.3 | 6.3 |

| | 9 Salmonella paratyphi ATCC 12176 | 10 P. mirabilis PM-444 | 11 Pseudo. aeruginosa HH 63 | 12 Serratia marcescens ATCC 13830 | 13 Proteus morgani 179 | 14 Enterobacter aerogenes ATCC 13048 | 15 Enterobacter cloacae HH 31254 |
|---|---|---|---|---|---|---|---|
| Pen G. | 0.8 | 1.6 | 200 | 2.5 | 200 | 12.5 | 6.3 |
| Cephalothin | 0.4 | 3.1 | >200 | >200 | >200 | 12.5 | 12.5 |
| Cefazolin | 0.4 | 3.1 | >200 | 100 | >200 | 0.8 | 0.8 |
| Ex. 45 | 3.1 | 50 | >200 | 200 | >200 | 2.5 | 25 |

What is claimed is:

1. A compound of the structure

in which:

A is azido, amino or blocked amino;

B is —CH$_2$X$^1$;

X$^1$ is OM, halo, methoxybenzylthio, triphenylmethylthio or mercapto;

M is hydrogen, lower alkylsulfonyl or phenylsulfonyl said phenyl being unsubstituted or substituted with a methyl or halo; and Z is hydrogen, 2,4-dimethoxybenzyl, benzhydryl or methoxy substituted benzhydryl.

2. The compound of claim 1 in which A is blocked amino, B is CH$_2$OH, and Z is hydrogen.

3. The compound of claim 2 in which A is t.-butoxycarbonylamino.

4. The compound of claim 1 in which A is t.-butoxycarbonylamino, B is —CH$_2$I and Z is hydrogen.

5. The compound of claim 1 in which A is t.-butoxycarbonylamino, B is —CH$_2$SH and Z is hydrogen.

6. The compound of claim 1 being cis-3-azido-2-tosyloxymethyl-4-oxoazetidine.

* * * * *